US010085951B2

(12) United States Patent
Gannon et al.

(10) Patent No.: US 10,085,951 B2
(45) Date of Patent: Oct. 2, 2018

(54) CURCUMINOID FORMULATIONS AND RELATED METHODS OF TREATMENT

(71) Applicant: DESIGNS FOR HEALTH, INC., Suffield, CT (US)

(72) Inventors: Sarah M. Gannon, Enfield, CT (US); Jose A. Llobrera, Belchertown, MA (US)

(73) Assignee: DESIGNS FOR HEALTH, INC., Suffield, CT (US)

( * ) Notice: Subject to any disclaimer, the term of this patent is extended or adjusted under 35 U.S.C. 154(b) by 15 days.

(21) Appl. No.: 14/962,684

(22) Filed: Dec. 8, 2015

(65) Prior Publication Data

US 2016/0166516 A1 Jun. 16, 2016

Related U.S. Application Data

(60) Provisional application No. 62/090,487, filed on Dec. 11, 2014.

(51) Int. Cl.
*A61K 31/12* (2006.01)
*A61K 9/48* (2006.01)

(52) U.S. Cl.
CPC ............ *A61K 31/12* (2013.01); *A61K 9/4858* (2013.01)

(58) Field of Classification Search
CPC .............................. A61K 31/12; A61K 9/4858
USPC ....................................................... 514/679
See application file for complete search history.

(56) References Cited

U.S. PATENT DOCUMENTS

| | | | |
|---|---|---|---|
| 5,266,344 A | 11/1993 | Mimura et al. | |
| 6,440,468 B1 | 8/2002 | Quintanilla Almagro et al. | |
| 6,797,470 B2 | 9/2004 | Barany et al. | |
| 7,060,733 B2 | 6/2006 | Pandol et al. | |
| 7,220,438 B2 | 5/2007 | Quintanilla Almagro et al. | |
| 7,682,636 B2 | 3/2010 | Babish et al. | |
| 7,736,679 B2 | 6/2010 | Antony | |
| 7,879,373 B2 | 2/2011 | Antony | |
| 7,883,728 B2 | 2/2011 | Antony | |
| 7,968,115 B2 | 6/2011 | Kurzrock et al. | |
| 8,153,172 B2 | 4/2012 | Antony | |
| 8,197,869 B2 | 6/2012 | Antony | |
| 8,329,233 B2 | 12/2012 | Antony | |
| 8,329,757 B2 | 12/2012 | Chen | |
| 8,440,245 B2 | 5/2013 | Johns et al. | |
| 8,487,139 B2 | 7/2013 | Raja et al. | |
| 8,568,802 B2 | 10/2013 | Gokaraju et al. | |
| 8,568,815 B2 | 10/2013 | Parkkinen | |
| 8,632,815 B2 | 1/2014 | Nair et al. | |
| 8,680,143 B2 | 3/2014 | Chaniyilparampu et al. | |
| 8,748,494 B2 | 6/2014 | Diaz Alperi et al. | |
| 8,772,265 B2 | 7/2014 | Neven et al. | |
| 8,785,380 B2 | 7/2014 | Madhavamenon | |
| 2008/0226755 A1 | 9/2008 | Antony | |
| 2010/0179103 A1 | 7/2010 | Desari | |
| 2010/0247734 A1 | 9/2010 | Johns et al. | |
| 2011/0160276 A1 | 6/2011 | Namboothiri et al. | |
| 2011/0190399 A1 | 8/2011 | Kar et al. | |
| 2011/0212142 A1 | 9/2011 | Chaniyilparampu et al. | |
| 2012/0207863 A1 | 8/2012 | Antony | |
| 2012/0220666 A1 | 8/2012 | Antony | |
| 2012/0288555 A1 | 11/2012 | Awasthi et al. | |
| 2013/0029905 A1 | 1/2013 | Madhavamenon et al. | |
| 2013/0143969 A1 | 6/2013 | Liu et al. | |
| 2013/0225689 A1 | 8/2013 | Khamar et al. | |
| 2014/0010903 A1 | 1/2014 | Madhavamenon et al. | |
| 2014/0031403 A1 | 1/2014 | Gately et al. | |
| 2014/0088200 A1 | 3/2014 | Antony | |
| 2014/0093594 A1 | 4/2014 | Antony | |
| 2014/0099390 A1 | 4/2014 | Antony | |
| 2014/0161915 A1 | 6/2014 | Payne et al. | |
| 2014/0193533 A1 | 7/2014 | Antony | |
| 2014/0228318 A1 | 8/2014 | Chauhan et al. | |
| 2014/0295005 A9 | 10/2014 | Anthony | |

OTHER PUBLICATIONS

Cuomo J, Appendino G, Dern AS, Schneider E, McKinnon TP, Brown MJ, Togni S, Dixon BM., Comparative absorption of a standardized curcuminoid mixture and its lecithin formulation., J Nat Prod. Apr. 25, 2011;74(4):664-9.doi: 10.1021/np1007262. Epub Mar. 17, 2011. PMID 21413691.

Shoba G, Joy D, Joseph T, Majeed M, Rajendran R, Srinivas PS., Influence of piperine on the pharmacokinetics of curcumin in animals and human volunteers., Planta Med. May 1998;64(4):353-6. PMID: 9619120.

Antony B, Merina B, Iyer VS, Judy N, Lennertz K, Joyal S., A Pilot Cross-Over Study to Evaluate Human Oral Bioavailability of BCM-95CG (Biocurcumax), A Novel Bioenhanced Preparation of Curcumin., Indian J Pharm Sci. Jul.-Aug. 2008;70(4):445-9. doi: 10.4103/0250-474X.44591. PMID: 20046768.

Schiborr C, Kocher A, Behnam D, Jandasek J, Toelstede S, Frank J., The oral bioavailability of curcumin from micronized powder and liquid micelles is significantly increased in healthy humans and differs between sexes., Mol Nutr Food Res. Mar. 2014;58(3):647 PMID: 24402825.

(Continued)

*Primary Examiner* — Kristin Ann Vajda
(74) *Attorney, Agent, or Firm* — Henry D. Coleman; Neil R. Sudol

(57) ABSTRACT

The invention provides novel curcuminoid formulations which have improved aqueous solubility and bioavailability when compared to known curcuminoid dosage forms. Formulations of the invention exhibit an enhanced intestinal absorption of curcuminoids, a slower curcuminoid metabolism and a reduced rate of systemic curcuminoid elimination. Additionally, upon administration in vivo, the formulations described and claimed herein produce a high, sustained level of the curcuminoid metabolite tetrahydrocurcumin. For example, at about eight to about ten hours after oral administration to a human, tetrahydrocurcumin plasma levels of between about 50 ng/mL to about 175 ng/mL are detectable, even when that metabolite is absent from the administered formulation. Novel processes for making curcuminoid formulations which have improved aqueous solubility and oral bioavailability, and methods of treating a wide variety of inflammatory, immune and neurogenerative disorders and cancers, are also provided.

20 Claims, 5 Drawing Sheets

(56) References Cited

OTHER PUBLICATIONS

Jäger R, Lowery RP, Calvanese AV, Joy, JM, Purpura M, Wilson JM., Comparative absorption of curcumin formulations. , Nutr J. Jan. 24, 2014;13:11. doi: 10.1186/1475-2891-13-11. PMID: 24461029.

Kada K, Wangpoengtrakul C, Tanaka T, Toyokuni S, Uchida K, Osawa T., Curcumin and especially tetrahydrocurcumin ameliorate oxidative stress-induced renal injury in mice. J Nutr. Aug. 2001;131(8):2090-5. PMID: 11481399.

Osawa T, Sugiyama Y, Inayoshi M, Kawakishi S., Antioxidative activity of tetrahydrocurcuminoids., Biosci Biotechnol Biochem. Sep. 1995;59(9):1609-12. PMID: 8520105.

Sugiyama Y, Kawakishi S, Osawa T., Involvement of the beta-diketone moiety in the antioxidative mechanism of tetrahydrocurcumin., Biochem Pharmacol. Aug. 23, 1996;52(4):519-25. PMID: 8759023.

Majeed M, Prakash L. , Tetrahydrocurcuminoids: Product write-up bioactive antioxidant compounds from curcuminoids., Sabinsa Corporation http://www.sabinsa.com/products/standardized-phytoextracts/tetrahydrocurcuminoids/tetrahydrocurcuminoids.pdf curcuminoids, Majeed M, Prakash L. Sabinsa Corporation http://www.sabinsa.com/products/standardized-phytoextracts/tetrahydrocurcuminoids/tetrahydrocurcuminoids.pdf.

Nakamura Y, Ohto Y, Murakami A, Osawa T, Ohigashi H. , Inhibitory effects of curcumin and tetrahydrocurcuminoids on the tumor promoter-induced reactive oxygen species generation in leukocytes in vitro and in vivo. , Jpn J Cancer Res. Apr. 1998;89(4):361-70. PMID: 9617340.

Wu JC, Tsai ML, Lai CS, Wang YJ, Ho CT, Pan MH., Chemopreventative effects of tetrahydrocurcumin on human diseases. Food Funct. Jan. 2014;5(1):12-7. doi: 10.1039/c3fo60370a. PMID: 24220621.

Lai CS, Wu JC, Yu SF, Badmaev V, Nagabhushanam K, Ho CT, Pan MH., 12. Tetrahydrocurcumin is more effective than curcumin in preventing azoxymethane-induced colon carcinogenesis., Mol Nutr Food Res. Dec. 2011;55(12):1819-28. doi: 10.1002/mnfr.201100290. Epub Sep. 2, 2011. PMID: 21887819.

Xiang L, Nakamura Y, Lim YM, Yamasaki Y, Kurokawa-Nose Y, Maruyama W, Osawa T, Matsuura A, Motoyama N, Tsuda L., 13. Tetrahydrocurcumin extends life span and inhibits the oxidative stress response by regulating the FOXO forkhead transcription factor., Aging (Albany NY). Nov. 2011;3(11):1098-109. PMID: 22156377.

Wright LE, Frye JB, Gorti B, Timmermann BN, Funk JL., Bioactivity of turmeric-derived curcuminoids and related metabolites in breast cancer. , Curr Pharm Des. 2013;19(34):6218-25. PMID: 23448448.

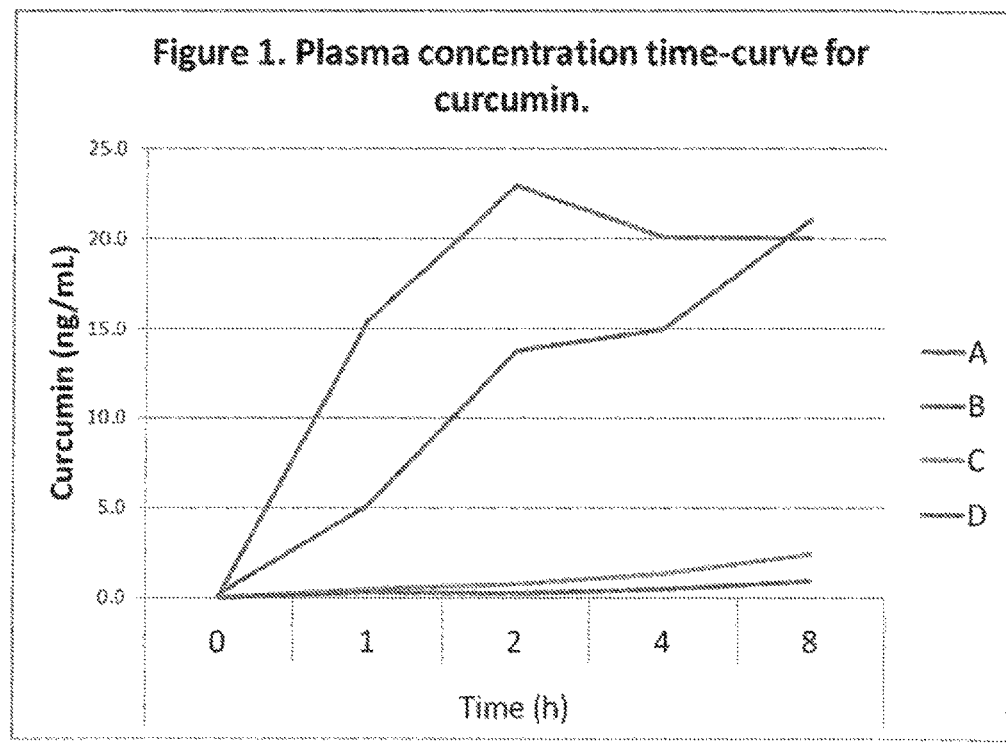

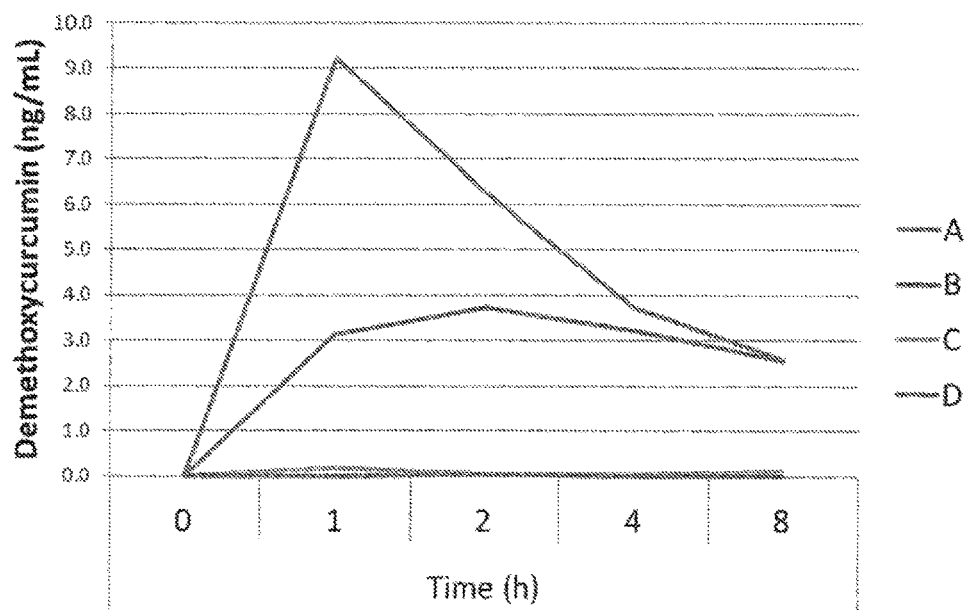

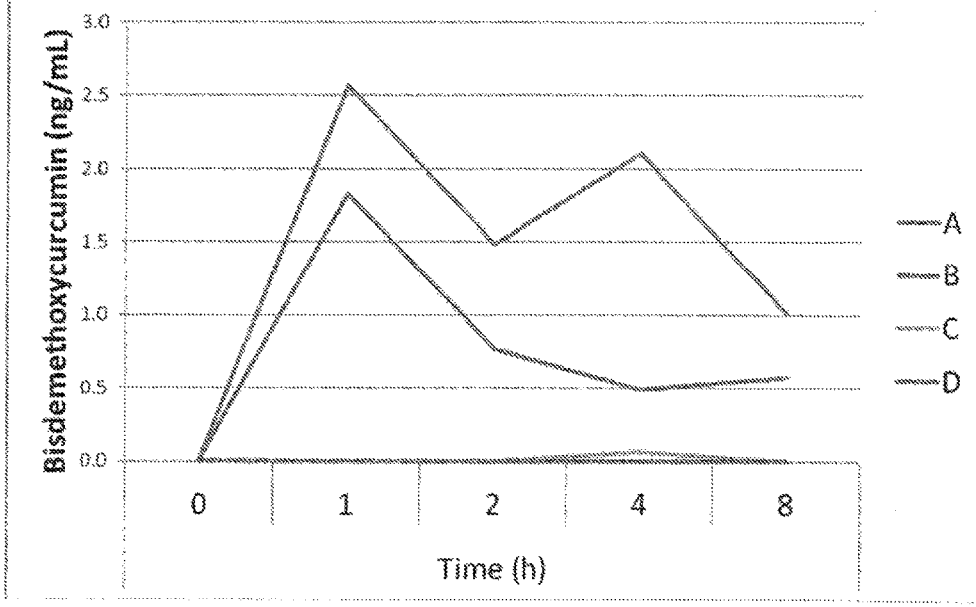

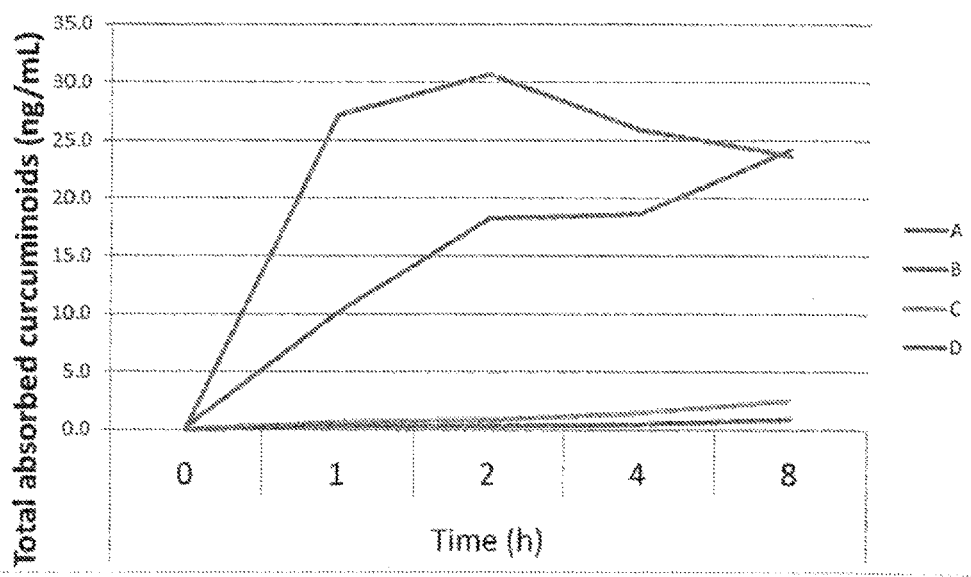

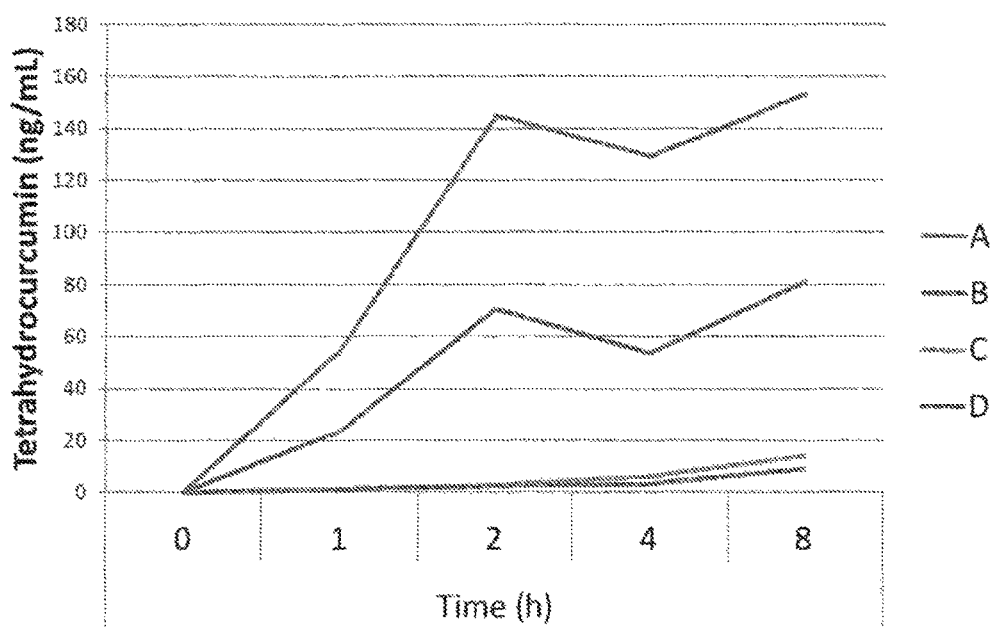
Figure 5. Plasma concentration time-curve for tetrahydrocurcumin.

CURCUMINOID FORMULATIONS AND RELATED METHODS OF TREATMENT

RELATED APPLICATIONS

This application claims the benefit of priority of provisional application No. 62/090,487, filed Dec. 11, 2014, of identical title, the entire contents of which are incorporated by reference in their entirety herein.

FIELD OF THE INVENTION

The invention provides novel curcuminoid formulations which have improved aqueous solubility and bioavailability when compared to known curcuminoid dosage forms. Formulations of the invention exhibit an enhanced intestinal absorption of curcuminoids, a slower curcuminoid metabolism and a reduced rate of systemic curcuminoid elimination. Additionally, upon administration in vivo, the formulations described and claimed herein produce a high, sustained level of the curcuminoid metabolite tetrahydrocurcumin. For example, at about eight to about ten hours after oral administration to a human, tetrahydrocurcumin plasma levels of between about 50 ng/mL to about 175 ng/mL are detectable, even when that metabolite is absent from the administered formulation.

Novel processes for making curcuminoid formulations which have improved aqueous solubility and bioavailability are also provided.

In other embodiments, the invention provides methods of treatment in which the novel curcuminoid formulations are used to treat and/or prevent a wide variety of inflammatory, immune and neurogenerative disorders and cancers. In certain preferred embodiments, the novel curcuminoid formulations are used to treat and/or prevent multiple myeloma, pancreatic cancer, myelodysplastic syndromes, colon cancer, psoriasis, arthritis, major depressive disorder and Alzheimer's disease, mild cognitive impairment and Alzheimer's prodrome, among others.

BACKGROUND OF THE INVENTION

Turmeric powder, extracts and oleoresins are some of the widely used commercial products of C. longa plant. Solvent extraction of dried turmeric rhizomes yields a mixture of three curcuminoids: curcumin (typically at a level of 90-95% purity), demethoxycurcumin and bisdemethoxycurcumin.

While curcumin and its metabolite tetrahydrocurcumin have demonstrated antioxidant, antiproliferative and antiangiogenic activities, extremely poor aqueous solubility limits the bioavailability and therapeutic effective of curcumin. Orally administered curcumin and tetrahydrocurcumin formulations have exhibited poor absorption, rapid metabolism, and rapid systemic elimination in vivo. As outlined in U.S. Patent Application Document No. 20140010903, efforts to improve the bioavailability of curcumin have included the use of adjuvants like piperine, liposomal and nanoparticulate formulations, phospholipid complexes and structural analogs.

Further examples of strategies which have been employed to improve curcumin bioavailability and solubility include (1) dispersion of curcumin in lipophilic matrix (Mereva®) (2) administering curcumin with piperine (Sabinsa) (3) combining curcumin with volatile oils of turmeric (BCM-95®), and (4) micronization and micellation of curcumin (Aquanova) [1-4].

Given curcumin's demonstrated anti-inflammatory, antioxidant, antiproliferative and antiangiogenic activities, the need exists for curcuminoid formulations which exhibit improved bioavailability and which are more readily formulated than known curcuminoid dosage forms.

SUMMARY OF THE INVENTION

We have developed novel pharmaceutical compositions which are preferably orally administered and which comprise one or more curcuminoids, curcuminoid analogs or curcuminoid metabolites and an absorption enhancer. Our pharmaceutical compositions exhibit improved aqueous solubility and bioavailability when compared to known curcuminoid dosage forms and facilitate the treatment and/or prevention of a wide variety of disorders, including inflammatory disorders, immune disorders, neurogenerative disorders and cancers.

In one embodiment, our invention provides a pharmaceutical composition comprising:
(a) a therapeutically effective amount of one or more curcuminoids, curcuminoid analogs or curcuminoid metabolites;
(b) an absorption enhancer;
(c) optionally, a water-in-oil emulsifier and/or essential oil of Curcuma longa L. (turmeric oil); and
(d) optionally, one or more additional, pharmaceutically-acceptable excipients;
wherein the weight percentage ratio of the one or more curcuminoids, curcuminoid analogs and/or curcuminoid metabolites to the absorption enhancer is between about 20:1 to about 1:60, or between about 15:1 to about 1:45, or between about 10:1 to about 1:40, or between about 9:1, 8:1, 7:1, 6:1, 5:1, 4:1, 3:1, 2:1 or 1:1 to about 1:2, 1:3, 1:4, 1:5, 1:6, 1:7, 1:8, 1:9, 1:10, 1:15, 1:20, 1:25, 1:30, or 1:35, and preferably is about 20:1, 19:1, 18:1, 17:1, 16:1, 15:1, 14:1, 13:1, 12:1, 11:1, 10:1, 9:1, 8:1, 7:1, 6:1 or 5:1.

In certain embodiments, the absorption enhancer is selected from the group consisting of chitosan, lecithin, lectin, a sucrose fatty acid ester, a water-soluble vitamin E derivative (preferably a polyalkylene glycol, preferably a polyethylene glycol or PEG derivative of vitamin E such as Vitamin E-TPGS) and mixtures thereof, and the water-in-oil emulsifier is selected from the group consisting of sorbitan derivatives such as sorbitan laurate and sorbitan palmitate; alkoxylated alcohols such as laureth-4; hydroxylated derivatives of polymeric silicones, such as dimethicone copolyol; alkylated derivatives of hydroxylated polymeric silicones, such as cetyl dimethicone copolyol; glyceryl esters such as polyglyceryl-4 isostearate; beeswax derivatives such as sodium isostearoyl-2-lactylate; lecithin; and mixtures thereof.

In a preferred embodiment, the invention provides a softgel or hard gel (preferably softgel) capsule comprising:
(a) between about 250 mg to about 1200 mg, or between about 300 mg to about 1100 mg, or about 325 mg to about 950 mg, most preferably about 380 mg of total curcuminoids;
(b) an absorption enhancing polyalkylene glycol derivative of vitamin E, preferably a PEG derivative of vitamin E as otherwise described herein, preferably selected from the group consisting of tocopheryl polyethylene glycol succinate (TPGS), tocopheryl polyethylene glycol sebacate, tocopheryl polyethylene glycol dodecanodioate, tocopheryl polyethylene glycol suberate, tocopheryl polyethylene glycol azelaate, tocopheryl polyethylene glycol citraconate, tocopheryl polyethylene glycol methylcitraconate, tocopheryl polyethylene glycol itaconate, tocopheryl polyethylene glycol maleate, tocopheryl polyethylene glycol glutarate, tocopheryl polyethylene glycol glutaconate, tocopheryl polyethylene glycol fumarate, tocopheryl polyethylene glycol phthalate, tocotrienol polyethylene glycol succinate, tocotrienol polyethylene glycol sebacate, tocotrienol polyethylene glycol dodecanodioate, tocotrienol polyethylene glycol suberate, tocotrienol polyethylene glycol azelaate, tocotrienol polyethylene glycol citraconate, tocotrienol polyethylene glycol methylcitraconate, tocotrienol polyethylene glycol itaconate, tocotrienol polyethylene glycol maleate, tocotrienol polyethylene glycol glutarate, tocotrienol polyethylene glycol glutaconate, tocotrienol polyethylene glycol fumarate and tocotrienol polyethylene glycol phthalate Vitamin E-TPGS and mixtures thereof, among others;

(c) optionally, lecithin; and (d) further optionally, one or more additional, pharmaceutically-acceptable excipients;

wherein (1) the total curcuminoids comprise between about 50 wt % to about 95 wt %, often about 65 wt % to about 90 wt % (preferably between about 75 wt % to about 85 wt %) of curcumin; between about 2 wt % to about 50 wt %, often about 10 wt % to about 30 wt % (preferably between about 15 wt % to about 20 wt %) of demethoxycurcumin; and between about 0.1 wt % to about 20 wt %, often about 2 wt % to about 8 wt % (most preferably about 5 wt %) of bisdemethoxycurcumin; and (2) the weight percentage ratio of the total curcuminoids to the absorption enhancer is between about 20:1, 19:1, 18:1, 17:1, 16:1, 15:1, 14:1, 13:1, 12:1, 11:1, 10:1, 9:1, 8:1, 7:1, 6:1, 5:1, 4:1, 3:1, 2:1 or 1:1.

Preferably, the softgel or hard gel capsule comprises:

(a) between about 0.5 wt % to about 30 wt %, about 1.0 wt % to about 20 wt %, about 2 wt % to about 8 wt % (most preferably about 5 wt %) of a polyalkylene glycol derivative of vitamin E (often a PEG derivative of vitamin E, more often, Vitamin E-TPGS);

(b) between about 0.5 wt % to about 50 wt %, often about 12 wt % to about 32 wt % (most preferably about 22 wt %) of lecithin; and (c) between about 0.5 wt % to about 60 wt %, often about 10 wt % to about 50 wt %, more often about 22 wt % to about 42 wt % (most preferably about 32 wt %) of essential oil of *Curcuma longa* L. (turmeric oil); and (d) optionally, one or more additional, pharmaceutically-acceptable excipients.

In certain embodiments of the pharmaceutical compositions of the invention, the total curcuminoids comprise between about 50 wt % to about 95 wt %, often about 65 wt % to about 90 wt % (preferably between about 75 wt % to about 85 wt %) of curcumin; between about 2 wt % to about 50 wt %, often about 10 wt % to about 30 wt % (preferably between about 15 wt % to about 20 wt %) of demethoxycurcumin; and between about 0.1 wt % to about 20 wt %, often about 2 wt % to about 8 wt % (most preferably about 5 wt %) of bisdemethoxycurcumin.

In a particularly preferred embodiment, the invention provides a softgel or hard gel capsule consisting of:

(a) between about 2 wt % to about 8 wt % (most preferably about 5 wt %) of Vitamin E-TPGS;

(b) between about 12 wt % to about 32 wt % (most preferably about 22 wt %) of lecithin;

(c) between about 22 wt % to about 42 wt % (most preferably about 32 wt %) of essential oil of *Curcuma longa* L. (turmeric oil);

(d) between about 250 mg to about 1200 mg, or between about 300 mg to about 1100 mg, or about 325 mg to about 950 mg, most preferably about 380 mg of total curcuminoids which consist essentially of about 65 wt % to about 90 wt % (preferably between about 75 wt % to about 85 wt %) of curcumin; between about 10 wt % to about 30 wt % (preferably between about 15 wt % to about 20 wt %) of demethoxycurcumin; and between about 2 wt % to about 8 wt % (most preferably about 5 wt %) of bisdemethoxycurcumin; and (e) optionally, one or more additional, pharmaceutically-acceptable excipients.

In certain other embodiments of the pharmaceutical compositions of the invention, the composition is a powder which consists of one or more curcuminoids, a water-soluble vitamin E derivative (preferably a polyalkylene glycol derivative of vitamin E and most preferably Vitamin E-TPGS) and, optionally, one or more additional, pharmaceutically-acceptable excipients.

Preferably, the powder consists of:

(a) between about 250 mg to about 1200 mg, or between about 300 mg to about 1100 mg, or about 325 mg to about 950 mg, most preferably about 380 mg of total curcuminoids;

(b) between about 2 wt % to about 8 wt % of the water-soluble vitamin E derivative (most preferably about 5 wt %); and (c) optionally, one or more additional, pharmaceutically-acceptable excipients.

In other preferred powder embodiments, the weight percentage ratio of the one or more curcuminoids, curcuminoid analogs and/or curcuminoid metabolites to the water-soluble vitamin E derivative is about 20:1.

In still other preferred powder embodiments, the total curcuminoids comprise between about 75 wt % to about 95 wt % curcumin (preferably between about 80 wt % to about 85 wt %); between about 5 wt % to about 25 wt % demethoxycurcumin (preferably between about 15 wt % to about 20 wt %); and between about 1 wt % to about 5 wt % (preferably about 3 wt %) bisdemethoxycurcumin.

In another particularly preferred embodiment, the invention provides a powder consisting of:

(a) between about 250 mg to about 1200 mg, or between about 300 mg to about 1100 mg, or about 325 mg to about 950 mg, most preferably about 380 mg of total curcuminoids which consist essentially of about 65 wt % to about 85 wt % (preferably between about 75 wt % to about 85 wt %) of curcumin, between about 10 wt % to about 30 wt % (preferably between about 15 wt % to about 20 wt %) of demethoxycurcumin and between about 2 wt % to about 8 wt % (most preferably about 5 wt %) of bisdemethoxycurcumin;

(b) Vitamin E-TPGS; and (c) optionally, one or more additional, pharmaceutically-acceptable excipients;

wherein the weight percentage ratio of the total curcuminoids to Vitamin E-TPGS is about 1:1, 2:1, 3:1, 4:1, 5:1, 6:1, 7:1, 8:1, 9:1, 10:1, 11:1, 12:1, 13:1, 14:1, 15:1, 16:1, 17:1, 18:1, 19:1 or 20:1.

In certain embodiments, at about eight to about ten hours after oral administration of a pharmaceutical composition of the invention to a human, tetrahydrocurcumin levels of between about 1 ng/ml to about 200 ng/ml, often 10 ng/ml to about 185 ng/ml, often about 50 ng/mL to about 175 ng/mL are detectable in plasma of the human, even where that metabolite is absent from the administered formulation. In certain preferred embodiments, tetrahydrocurcumin levels of between about 50 ng/mL to about 175 ng/mL are detectable in the plasma of the patient or subject, even where that metabolite is absent or substantially absent from the administered formulation. It is noted that approximately the same (or a slightly reduced) concentration of tetrahydrocurcumin is found in the serum, any difference occurring as a consequence of processing of plasma to produce serum (serum differs from plasma in that it does not contain fibrinogen and clotting factors).

In still other preferred embodiments, the pharmaceutical composition is a softgel or hard gel capsule (preferably softgel) which comprises a curcuminoid powder as described above.

In still other embodiments, the invention provides a method of treating and/or preventing one or more disorders selected from the group consisting of an inflammatory disorder, an immune disorder, a neurogenerative disorder and a cancer, the method comprising administering to a subject in need thereof a therapeutically effective amount of a pharmaceutical composition of the invention as described above. In certain embodiments, the subject suffers from, or is at risk of developing, one or more disorders selected from the group consisting of multiple myeloma, pancreatic cancer, myelodysplastic syndromes, colon cancer, psoriasis, arthritis, major depressive disorder and/or Alzheimer's disease.

In still other embodiments, the invention provides a process for making a curcuminoid formulation which has improved aqueous solubility and bioavailability, the process comprising:
(a) melting a water-soluble vitamin E derivative (preferably a polyalkylene glycol derivative of vitamin E and most preferably Vitamin E-TPGS) at a temperature of between about 65° C.-70° C.;
(b) adding one or more curcuminoids, curcuminoid analogs and/or curcuminoid metabolites, optionally in the presence of a non-aqueous solvent or mixture of solvents, or alternatively, in an aqueous solvent, under agitation to the melted water-soluble vitamin E derivative to form a non-aqueous solution (for formulation in a softgel capsule) or a substantially uniformly-mixed slurry (for producing a powder after drying for formulation in tablets and/or capsules); and, optionally
(c) drying the substantially uniformly-mixed slurry by evaporation or lyophilization to form a powder;
wherein the weight percentage ratio of the one or more curcuminoids, curcuminoid analogs and/or curcuminoid metabolites to the water-soluble vitamin E derivative in said non-aqueous solution or said slurry is between about 20:1 to about 1:60, or between about 15:1 to about 1:45, or between about 10:1 to about 1:40, or between about 9:1, 8:1, 7:1, 6:1, 5:1, 4:1, 3:1, 2:1 or 1:1 to about 1:2, 1:3, 1:4, 1:5, 1:6, 1:7, 1:8, 1:9, 1:10, 1:15, 1:20, 1:25, 1:30, or 1:35, and preferably is about 20:1, 19:1, 18:1, 17:1, 16:1, 15:1, 14:1, 13:1, 12:1, 11:1, 10:1, 9:1, 8:1, 7:1, 6:1 or 5:1.

While not wishing to be bound by any theory, we believe that although there is no evidence that a water-soluble vitamin E derivative such as Vitamin E-TPGS reacts with one or more curcuminoids in our formulations to form the metabolite tetrahydrocurcumin prior to administration, the absorption-enhancing water-soluble vitamin E derivative may very well react synergistically with the curcuminoids in vivo by enhancing curcuminoid reduction to yield increased serum/plasma levels of tetrahydrocurcumin.

These and other aspects of our invention are described in further detail in the Detailed Description of the Invention.

BRIEF DESCRIPTION OF THE FIGURES

FIGS. 1-5 are concentration time-curves illustrating mean curcuminoid plasma concentrations determined in the experiment(s) of Example 2. Concentrations are expressed in ng/mL and refer to enzymatically hydrolyzed plasma samples. Formulation A was a softgel formulated according to the invention described and claimed herein (see Example 1), Formulation B was a powder formulated according to the invention described and claimed herein in hard gel capsule (see Example 1), Formulation C was a commercially available curcumin powder (95 wt % curcuminoids) in hard gel capsule and Formulation D was a commercially available curcumin hard gel capsule.

DETAILED DESCRIPTION OF THE INVENTION

It is noted that, as used in this specification and the appended claims, the singular forms "a," "an," and "the," include plural referents unless expressly and unequivocally limited to one referent. Thus, for example, reference to "a compound" includes two or more different compound. As used herein, the term "include" and its grammatical variants are intended to be non-limiting, such that recitation of items in a list is not to the exclusion of other like items that can be substituted or other items that can be added to the listed items.

The term "compound" or "agent", as used herein, unless otherwise indicated, refers to any specific chemical compound (e.g. curcuminoid) disclosed herein and includes tautomers, regioisomers, geometric isomers as applicable, and also where applicable, optical isomers (e.g. enantiomers) thereof, as well as pharmaceutically acceptable salts thereof. Within its use in context, the term compound generally refers to a single compound, but also may include other compounds such as stereoisomers, regioisomers and/or optical isomers (including racemic mixtures) as well as specific enantiomers or enantiomerically enriched mixtures of disclosed compounds as well as diastereomers and epimers, where applicable in context. The term also refers, in context to prodrug forms of compounds which have been modified to facilitate the administration and delivery of compounds to a site of activity.

The term "patient" or "subject" is used throughout the specification within context to describe an animal, generally a mammal, including a domesticated mammal including a farm animal (dog, cat, horse, cow, pig, sheep, goat, etc.) and preferably a human, to whom treatment, including prophylactic treatment (prophylaxis), with the methods and compositions according to the present invention is provided. For treatment of those conditions or disease states which are specific for a specific animal such as a human patient, the term patient refers to that specific animal, often a human.

The terms "effective" or "pharmaceutically effective" are used herein, unless otherwise indicated, to describe an amount of a compound or composition which, in context, is used to produce or affect an intended result, usually the modulation of secretive or degradative autophagy within the context of a particular treatment or alternatively, the effect of a bioactive agent which is coadministered with the secretive or degradative autophagy modulator in the treatment of disease.

The terms "treat", "treating", and "treatment", etc., as used herein, refer to any action providing a benefit to a patient at risk for or afflicted by a secretive or degradative autophagy mediated disease state or condition as otherwise described herein. The benefit may be in curing the disease state or condition, inhibition its progression, or ameliorating, lessening or suppressing one or more symptom of a secretive autophagy mediated disease state or condition. Treatment, as used herein, encompasses both prophylactic and therapeutic treatment.

The term "co-administration" or "combination therapy" is used to describe a therapy in which at least two active compounds in effective amounts are used to treat a disorder as otherwise described herein, either at the same time or within dosing or administration schedules defined further herein or ascertainable by those of ordinary skill in the art. Although the term co-administration preferably includes the administration of at least two active compounds to the patient at the same time, it is not necessary that the compounds be administered to the patient at the same time, although effective amounts of the individual compounds will be present in the patient at the same time. In addition, in certain embodiments, co-administration will refer to the fact that two or more compounds are administered at significantly different times, but the effects of the two compounds are present at the same time.

The natural diaryl heptanoid "curcumin" (1,6-heptadiene-3,5-dione1,7-bis (4-hydroxy-3-methoxyphenyl)-(1E,6E)) is the principal "curcuminoid" and is derived from *Curcuma longa* L. (turmeric), a member of the Zingiberaceae family, a genus of rhizomateous herbs. Turmeric constituents include the three curcuminoids: curcumin (diferuloylmethane, the primary constituent and the one responsible for its vibrant yellow color), demethoxycurcumin, and bisdemethoxycurcumin, as well as volatile oils (tumerone, atlantone, and zingiberone) ("essential oil of *Curcuma longa* L. (turmeric oil)"), sugars, proteins, and resins.

Curcumin is a bis-α, β-unsaturated β-diketone and exists in equilibrium with its enol tautomer. The bis-keto form predominates in acidic and neutral aqueous solutions as well as in the cell. Curcumin is practically insoluble in water and ether but is soluble in ethanol, dimethylsulfoxide and acetone. An active metabolite of curcumin, tetrahydrocurcumin (a reduced form of curcumin), has a distinct advantage over the regular curcuminoids in that it has a higher bioavailability. Mechanistically, the regular curcuminoids once ingested, reach the intestine, where they need to pass through the absorption barrier to enter the biological system. The reductase system at the cellular level converts curcumin to tetrahydrocurcumin. In certain embodiments of the present invention, a desirable result is that an unexpectedly high percentage of the curcuminoids and in particular curcumin, is converted to tetrahydrocurcumin, providing the compositions with an increased bioavailability compared to compositions where curcumin is converted to tetrahydrocurcumin at a lower percentage, often in a far lower percentage than in the present invention.

The predominant curcuminoid metabolic pathways are reduction and conjugation; drug metabolizing enzymes such as alcohol dehydrogenase, UDP-glucuronosyltransferases (UGTs) or sulfotransferases (SULTs) may be involved in curcuminoid metabolic reactions. Besides the major metabolic pathways, dehydroxylation, cyclization and methylation can also occur in vivo. More than thirty metabolites of curcuminoids have been identified in biological matrices including the plasma, urine and bile from rats or humans; metabolites such as tetrahydrocurcuminoids have been reported to be active. Wang, et al., "Curcuminoid metabolism and its contribution to the pharmacological effects", *Curr Drug Metab*. 2013 September; 14(7):791-806. Such compositions are non-limiting examples of the "curcuminoid metabolites" which may be used in the formulations and methods of treatment of the invention.

While curcumin has been shown to be safe in human dosages of up to 10 g per day and to possess potent anti-inflammatory and anti-cancer activities, see Yang, et al. "Natural compounds with proteasome inhibitory activity for cancer prevention and treatment", *Curr Protein Pept Sci.* 2008 June; 9(3):227-39, its clinical application to date has been limited by its rapid metabolism and poor intestinal absorption (around 75% of orally ingested curcumin is excreted in the feces). In an effort to improve curcumin's oral bioavailability and aqueous solubility, a large number of curcuminoid analogs have been synthesized through aromatic ring substitutions and modifications of the β-diketone moiety and two flanking double bonds conjugated to the β-diketone moiety. See Vyas, et al., "Perspectives on new synthetic curcumin analogs and their potential anticancer properties", *Curr Pharm Des*. 2013; 19(11):2047-69. Such compositions are non-limiting examples of the "curcuminoid analogs" which may be used in the formulations and methods of treatment of the invention.

"Absorption enhancers" include, but are not limited to, chitosan, lecithin, lectin, a sucrose fatty acid ester, a water-soluble vitamin E derivative, preferably a polyalkylene glycol derivative of vitamin E, preferably a PEG derivative of vitamin E.

A "PEG derivative of Vitamin E" is a compound containing one or more Vitamin E moieties (e.g., a tocopherol or tocotrienol) joined together, for example by an ester, ether, amide or thioester bond, with one or more polyethylene glycol (PEG) moieties, the vitamin E moiety and the PEG group being joined via a linker, for example, a dicarboxylic or tricarboxylic acid or other bifunctional compound (often with two functional electrophilic groups). Exemplary PEG derivatives of Vitamin E are tocopherol polyethylene glycol succinate (TPGS), TPGS analogs, TPGS homologs and TPGS derivatives, as otherwise described herein.

The term "tocopherol polyethylene glycol diester" and "TPGD" refer to a PEG-derivative of tocopherol where the linker is a dicarboxylic acid (a carboxylic acid having two carboxy groups, e.g., succinic acid), such as succinic acid. Exemplary dicarboxylic acids that can be used as linkers in these tocopherol and tocotrienol PEG diester surfactants are succinic acid, sebacic acid, dodecanedioic acid, suberic acid, or azelaic acid, citraconic acid, methylcitraconic acid, itaconic acid, maleic acid, glutaric acid, glutaconic acid, fumaric acids and phthalic acids. Exemplary of the TPGDs are tocopherol succinate polyethylene glycol (TPGS, a preferred vitamin E derivative for use in the present invention), tocopherol sebacate polyethylene glycol, tocopherol dodecanodioate polyethylene glycol, tocopherol suberate polyethylene glycol, tocopherol azelaate polyethylene glycol, tocopherol citraconate polyethylene glycol, tocopherol methylcitraconate polyethylene glycol, tocopherol itaconate polyethylene glycol, tocopherol maleate polyethylene glycol, tocopherol glutarate polyethylene glycol, tocopherol glutaconate polyethylene glycol, and tocopherol phthalate polyethylene glycol, among others.

The terms "tocopherol polyethylene glycol succinate", "TPGS", "tocopheryl polyethylene glycol succinate surfactant" and "TPGS surfactant" refer to tocopherol polyethylene glycol (PEG) diesters, that are formed by joining, via esterification, tocopherol succinate, which itself is an ester made by esterification of tocopherol and succinic acid. The term tocopherol refers to any naturally occurring or synthetic form of vitamin E, and can refer to a single compound or a mixture. Examples of tocopherols include, for example, alpha.-tocopherol, D-alpha.-tocopherol, beta-tocopherol, gamma-tocopherol and delta-tocopherol. The PEG moiety of the TPGS surfactant can be any PEG moiety, for example, PEG moieties of a molecule weight between about 200 kDa and about 20,000 kDa typically between about 200 kDa and 6000 kDa (including about 200 kDA or about 6000 kDa), for example, between about 500 kDa and 5000 kDa, typically between about 200 kDa and 2000 kDa, between about 500 kDa and 1500 kDa, or between 500 kDa and about 1000 kDa, about 200 kDa, about 300 kDA, about 400 kDa, about 500 kDa, about 600 kDa, about 700 kDa, about 800 kDa, about 850 kDa, about 900 kDA, about 950 kDA, about 1000 kDa, about 1050 kDA, about 1100 kDA, about 1200 kDA, about 1300 kDA, about 1400 kDA, about 1500 kDA; and PEG moieties that are modified, for example, methylated PEG (m-PEG) and/or PEG moieties including other PEG analogs, e.g., PEG-NHS, PEG-aldehyde, PEG-SH, PEG-NH$_2$, PEG-CO$_2$H, and branched PEGs. Typically, the TPGS surfactant is GRAS (Generally Recognized As Safe). Preferred PEG moieties range in size from about 500 kDA to about 5,000 kDA, often about 500 kDA to about 2500 kDA, about 750 kDA to about 2000 kDA, about 1000 to about 2000 kDA, about 1000 to about 1500 kDC, about 1000 kDA, about 1500 kDA, about 2000 kDA, about 2500 kDA.

Exemplary of the TPGS surfactants is TPGS-1000, which has a PEG moiety of 1000 kDa (PEG 1000) and is a preferred PEG derivative of vitamin E for use in the present invention. The TPGS can be any natural, water-soluble, tocopherol polyethylene glycol succinate, for example, the food grade TPGS sold under the name Eastman Vitamin E TPGS, food grade, by Eastman Chemical Company, Kingsport, Tenn. This TPGS is water-soluble form of natural-source vitamin E, which is prepared by esterifying the carboxyl group of crystalline d-alpha-tocopheryl acid succinate with polyethylene glycol 1000 (PEG 1000), and contains between 260 and 300 mg/g total tocopherol. TPGS typically has a reported HLB value of between 12 or 13 or about 12 or 13 and 18 or about 18.

The terms "tocopherol polyethylene glycol succinate analog", "TPGS analog", and "TPGS analog surfactant" refer to compounds, other than TPGS, that are similar to a parent TPGS compound, but differ slightly in composition, for example, by the variation, addition or removal of an atom, one or more units (e.g., methylene unit(s)—$(CH_2)_n$) or one or more functional groups. TPGS analogs include Vitamin E derived surfactants, including PEG derivatives of Vitamin E, including vitamin E PEG diesters, such as, but not limited to, tocopherol polyethylene glycol sebacate (PTS), tocopherol polyethylene glycol dodecanodioate (PTD), tocopherol polyethylene glycol suberate (PTSr), tocopherol polyethylene glycol azelaate (PTAz), and polyoxyethanyl tocotrienyl sebacate (PTrienS) as well as other PEG derivatives of Vitamin E.

Exemplary of TPGS analogs are compounds, other than TPGS compounds, having the formula I shown below:

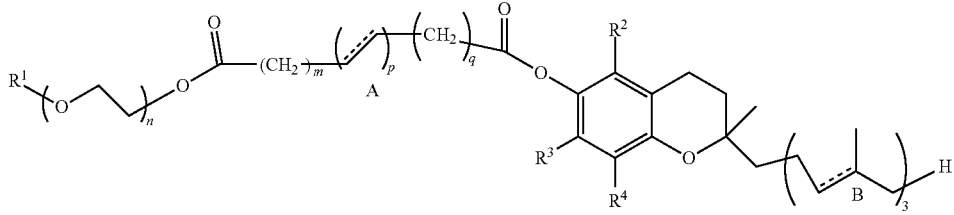

I where $R^1$, $R^2$, $R^3$ and $R^4$ are each independently H or Me, each dashed line is, independently, a single or double bond; n is an integer from 1 to 5,000; m and q are each independently 0 or 1; and p is an integer from 1-20. For example, TPGS analogs include, but are not limited to, compounds having the formula above, where, when the bonds represented by the dashed lines marked by "A" and "B" are single bonds, and m and q each equal 0, p is any integer from 2-20. TPGS analogs also include compounds where the dashed line at B or the dashed line at A, or both the dashed lines, represents at least one double bond. For example, TPGS analogs include a compound as in formula I, where when the dashed line in A represents only single bonds, the dashed line in "B" represents one or more double bond, e.g., tocotrienol PEG diesters. TPGS analogs also include compounds as in formula I, above, where when the dashed line marked "B" represents only single bonds, the dashed line marked "A" represents one or more double bonds; or when the dashed line labeled "A" does not represent double bonds, and m and q are each zero, p is greater than 1.

Also exemplary of TPGS analogs are compounds, other than TPGS compounds, having the formula II, below:

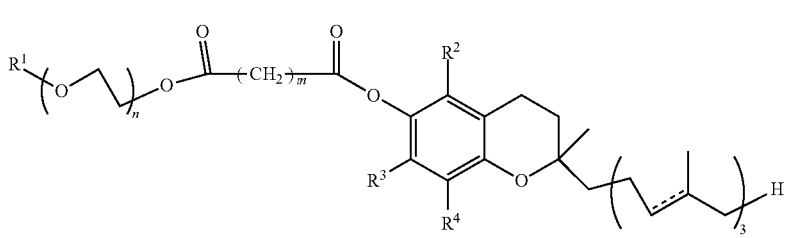

II where $R^1$, $R^2$, $R^3$ and $R^4$ are each independently H or Me, each dashed line is, independently, a single or double bond; n is an integer from 1 to 5,000; and m is an integer from 1 to 20.

Also exemplary of TPGS analogs include compounds other than TPGS, having PEG moieties that vary in chain length, according to formula III, below:

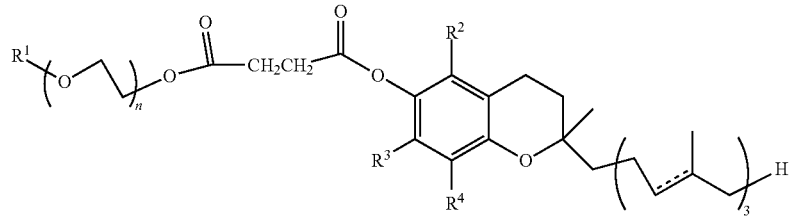

where $R^1$, $R^2$, $R^3$ and $R^4$ are each independently H or Me, each dashed line is, independently, a single or double bond and n is an integer from among 1-5000.

The term "TPGS-1000 analogs" are compounds other than TPGS-1000 that are similar to a parent TPGS-1000 compound, but differ slightly in composition, for example, by the variation, addition or removal of an atom, one or more units (e.g., methylene unit(s)—$(CH_2)_n$) or one or more functional groups. Suitable TPGS-1000 analogs include, but are not limited to, other TPGS compounds, having PEG moiety(ies) that vary in chain length and molecular weight compared to TPGS-1000, including, for example, TPGS compounds having PEG moieties between 200 or about 200 kDa and 20,000 kDa or about 20,000 kDa, typically between 200 kDa or about 200 kDa and 6000 kDa or about 6000 kDa, for example, between 600 kDa or about 600 kDa and 6000 kDa or about 6000 kDa, typically between 200 kDa or about 200 kDa and 2,000 kDa or about 2,000 kDa, between 600 kDa or about 600 kDa and 1500 kDa or about 1500 kDa, such as, but not limited to, 200, 300, 400, 500, 600, 800, and 1000 kDa. Also exemplary of TPGS-1000 analogs are TPGS compounds having PEG moieties that are modified, for example, methylated PEG (m-PEG) and/or PEG moieties including other PEG analogs, e.g., PEG-NHS, PEG-aldehyde, PEG-SH, PEG-$NH_2$, PEG-$CO_2H$, and branched PEGs. Also exemplary of TPGS-1000 analogs are any TPGS analogs, e.g., Vitamin E derived surfactants, including PEG derivatives of Vitamin E, including vitamin E PEG diesters, such as, but not limited to, tocopherol polyethylene glycol sebacate (PTS), tocopherol polyethylene glycol dodecanodioate (PTD), tocopherol polyethylene glycol suberate (PTSr), tocopherol polyethylene glycol azelaate (PTAz) and polyoxyethanyl tocotrienyl sebacate (PTrienS) as well as other PEG derivatives of Vitamin E.

As used herein, "TPGS homologs" are analogs of TPGS that differ from a TPGS parent compound only by the presence or absence of a simple unit, such as a methylene unit, or some multiple of such units, e.g., —$(CH_2)_n$—. Typically, suitable TPGS homologs have similar surfactant properties compared to the parent compound (TPGS), for example, similar HLB values, for example, HLB values between 12 or 13 or about 12 or about 13 and 20 or about 20. Exemplary of TPGS homologs are tocopherol polyethylene glycol sebacate (PTS), tocopherol polyethylene glycol dodecanodioate (PTD), tocopherol polyethylene glycol suberate (PTSr), tocopherol polyethylene glycol azelaate (PTAz). Exemplary of TPGS homologs are compounds having the formula I (above), where neither the A or B dashed line represents a double bond and where, when m and q each are 0, p is greater than 1.

"TPGS-1000 homologs" are analogs of TPGS-1000 that differ from a TPGS-1000 parent compound only by the presence or absence of a simple unit, such as a methylene unit, or some multiple of such units, e.g., —$(CH_2)_n$—. Exemplary TPGS-1000 homologs have similar surfactant properties compared to the parent compound (TPGS-1000), for example, similar HLB values, for example, HLB values between 12, 13, or 14 or about 12, 13 or 14 and 18, 19 or 20 or about, 18, 19 or 20. Exemplary TPGS-1000 homologs include TPGS-1000 homologs with slight variations in the length of the PEG chain moiety, and me-TPGS-1000, which is a TPGS-1000 having a methyl cap on the PEG moiety.

Preferred PEG derivatives of vitamin E for use in the present invention are selected from the group consisting of tocopheryl polyethylene glycol succinate (TPGS), tocopheryl polyethylene glycol sebacate, tocopheryl polyethylene glycol dodecanodioate, tocopheryl polyethylene glycol suberate, tocopheryl polyethylene glycol azelaate, tocopheryl polyethylene glycol citraconate, tocopheryl polyethylene glycol methylcitraconate, tocopheryl polyethylene glycol itaconate, tocopheryl polyethylene glycol maleate, tocopheryl polyethylene glycol glutarate, tocopheryl polyethylene glycol glutaconate, tocopheryl polyethylene glycol fumarate, tocopheryl polyethylene glycol phthalate, tocotrienol polyethylene glycol succinate, tocotrienol polyethylene glycol sebacate, tocotrienol polyethylene glycol dodecanodioate, tocotrienol polyethylene glycol suberate, tocotrienol polyethylene glycol azelaate, tocotrienol polyethylene glycol citraconate, tocotrienol polyethylene glycol methylcitraconate, tocotrienol polyethylene glycol itaconate, tocotrienol polyethylene glycol maleate, tocotrienol polyethylene glycol glutarate, tocotrienol polyethylene glycol glutaconate, tocotrienol polyethylene glycol fumarate and tocotrienol polyethylene glycol phthalate and mixtures thereof. Vitamin E-TPGS is a particularly preferred "absorption enhancer" having a PEG moiety ranging in size from about 500 kDA to about 2500 kDA, often about 1000 kDA to about 2000 kDA, "Water-in-oil emulsifiers" include, but are not limited to, sorbitan derivatives such as sorbitan laurate and sorbitan palmitate; alkoxylated alcohols such as laureth-4; sssshydroxylated derivatives of polymeric silicones, such as dimethicone copolyol; alkylated derivatives of hydroxylated polymeric silicones, such as cetyl dimethicone copolyol; glyceryl esters such as polyglyceryl-4 isostearate; beeswax derivatives such as sodium isostearoyl-2-lactylate; lecithin; and mixtures thereof. Lecithin is a particularly preferred "water-in-oil emulsifier".

An "inflammatory disorder" includes, but is not limited to, lung diseases, hyperglycemic disorders including diabetes and disorders resulting from insulin resistance, such as Type I and Type II diabetes, as well as severe insulin resistance, hyperinsulinemia, and dyslipidemia (e.g. hyperlipidemia (e.g., as expressed by obese subjects), elevated low-density lipoprotein (LDL), depressed high-density lipoprotein (HDL), and elevated triglycerides) and insulin-resistant diabetes, such as Mendenhall's Syndrome, Werner Syndrome, leprechaunism, and lipoatrophic diabetes, renal disorders, such as acute and chronic renal insufficiency, end-stage chronic renal failure, glomerulonephritis, interstitial nephritis, pyelonephritis, glomerulosclerosis, e.g., Kimmelstiel-Wilson in diabetic patients and kidney failure after kidney transplantation, obesity, GH-deficiency, GH resistance, Turner's syndrome, Laron's syndrome, short stature, increased fat mass-to-lean ratios, immunodeficiencies including decreased $CD4^+$ T cell counts and decreased immune tolerance or chemotherapy-induced tissue damage, bone marrow transplantation, diseases or insufficiencies of cardiac structure or function such as heart dysfunctions and congestive heart failure, neuronal, neurological, or neuromuscular disorders, e.g., diseases of the central nervous system including Alzheimer's disease, or Parkinson's disease or multiple sclerosis, and diseases of the peripheral nervous system and musculature including peripheral neuropathy, muscular dystrophy, or myotonic dystrophy, and catabolic states, including those associated with wasting caused by any condition, including, e.g., mental health condition (e.g., anorexia nervosa), trauma or wounding or infection such as with a bacterium or human virus such as HIV, wounds, skin disorders, gut structure and function that need restoration, and so forth.

"Inflammatory disorder" also includes a cancer and an "infectious disease" as defined herein, as well as disorders of bone or cartilage growth in children, including short stature, and in children and adults disorders of cartilage and bone in children and adults, including arthritis and osteoporosis. An "inflammation-associated metabolic disorder" includes a combination of two or more of the above disorders (e.g., osteoporosis that is a sequela of a catabolic state). Specific disorders of particular interest targeted for treatment herein are diabetes and obesity, heart dysfunctions, kidney disorders, neurological disorders, bone disorders, whole body growth disorders, and immunological disorders.

In one embodiment, an "inflammatory disorder" includes central obesity, dyslipidemia including particularly hypertriglyceridemia, low HDL cholesterol, small dense LDL particles and postpranial lipemia; glucose intolerance such as impaired fasting glucose; insulin resistance and hypertension, and diabetes. The term "diabetes" is used to describe diabetes mellitus type I or type II. The present invention relates to a method for improving renal function and symptoms, conditions and disease states which occur secondary to impaired renal function in patients or subjects with diabetes as otherwise described herein. It is noted that in diabetes mellitus type I and II, renal function is impaired from collagen deposits, and not from cysts in the other disease states treated by the present invention.

A "neurodegenerative disorder" or "neuroinflammation" includes, but is not limited to, Alzheimer's Dementia (AD), mild cognitive impairment, Alzheimer's prodrome, amyotrophic lateral sclerosis, depression, epilepsy, Huntington's Disease, multiple sclerosis, the neurological complications of AIDS, spinal cord injury, glaucoma and Parkinson's disease.

The term "cancer" is used throughout the specification to refer to the pathological process that results in the formation and growth of a cancerous or malignant neoplasm, i.e., abnormal tissue that grows by cellular proliferation, often more rapidly than normal and continues to grow after the stimuli that initiated the new growth cease. Cancers generally show partial or complete lack of structural organization and functional coordination with the normal tissue and most invade surrounding tissues, metastasize to several sites, and are likely to recur after attempted removal and to cause the death of the patient unless adequately treated. As used herein, the term cancer is used to describe all cancerous disease states applicable to treatment according to the present invention and embraces or encompasses the pathological process associated with all virtually all epithelial cancers, including carcinomas, malignant hematogenous, ascitic and solid tumors. Examples of cancers which may be treated using methods according to the present invention include, without limitation, carcinomas (e.g., squamous-cell carcinomas, adenocarcinomas, hepatocellular carcinomas, and renal cell carcinomas), particularly those of the bladder, bowel, breast, cervix, colon, esophagus, head, kidney, liver, lung, neck, ovary, pancreas, prostate, and stomach; leukemias; benign and malignant lymphomas, particularly Burkitt's lymphoma and Non-Hodgkin's lymphoma; benign and malignant melanomas; myeloproliferative diseases; sarcomas, particularly Ewing's sarcoma, hemangiosarcoma, Kaposi's sarcoma, liposarcoma, myosarcomas, peripheral neuroepithelioma, and synovial sarcoma; tumors of the central nervous system (e.g., gliomas, astrocytomas, oligodendrogliomas, ependymomas, gliobastomas, neuroblastomas, ganglioneuromas, gangliogliomas, medulloblastomas, pineal cell tumors, meningiomas, meningeal sarcomas, neurofibromas, and Schwannomas); germ-line tumors (e.g., bowel cancer, breast cancer, prostate cancer, cervical cancer, uterine cancer, lung cancer, ovarian cancer, testicular cancer, thyroid cancer, astrocytoma, esophageal cancer, pancreatic cancer, stomach cancer, liver cancer, colon cancer, and melanoma); mixed types of neoplasias, particularly carcinosarcoma and Hodgkin's disease; and tumors of mixed origin, such as Wilms' tumor and teratocarcinomas. See, for example, The Merck Manual of Diagnosis and Therapy, 17.sup.th ed. (Whitehouse Station, N.J.: Merck Research Laboratories, 1999) 973-74, 976, 986, 988, 991).

In addition to the treatment of ectopic cancers as described above, the present invention also may be used preferably to treat eutopic cancers such as choriocarcinoma, testicular choriocarcinoma, non-seminomatous germ cell testicular cancer, placental cancer (trophoblastic tumor) and embryonal cancer, among others.

An "immune disorder" includes, but is not limited to, lupus, multiple sclerosis, rheumatoid arthritis, psoriasis, Type I diabetes, complications from organ transplants, xeno transplantation, diabetes, cancer, asthma, atopic dermatitis, autoimmune thyroid disorders, ulcerative colitis, Crohn's disease, Alzheimer's disease and leukemia.

The term "additional anticancer agent" shall mean chemotherapeutic agents such as an agent selected from the group consisting of microtubule-stabilizing agents, microtubule-disruptor agents, alkylating agents, antimetabolites, epidophyllotoxins, antineoplastic enzymes, topoisomerase inhibitors, inhibitors of cell cycle progression, and platinum coordination complexes. These may be selected from the group consisting of everolimus, trabectedin, abraxane, TLK 286, AV-299, DN-101, pazopanib, GSK690693, RTA 744, ON 0910.Na, AZD 6244 (ARRY-142886), AMN-107, TKI-258, GSK461364, AZD 1152, enzastaurin, vandetanib, ARQ-197, MK-0457, MLN8054, PHA-739358, R-763, AT-9263, a FLT-3 inhibitor, a VEGFR inhibitor, an EGFR TK inhibitor, an aurora kinase inhibitor, a PIK-1 modulator, a Bcl-2 inhibitor, an HDAC inhbitor, a c-MET inhibitor, a PARP inhibitor, a Cdk inhibitor, an EGFR TK inhibitor, an IGFR-TK inhibitor, an anti-HGF antibody, a PI3 kinase inhibitors, an AKT inhibitor, a JAK/STAT inhibitor, a checkpoint-1 or 2 inhibitor, a focal adhesion kinase inhibitor, a Map kinase kinase (mek) inhibitor, a VEGF trap antibody, pemetrexed, erlotinib, dasatanib, nilotinib, decatanib, panitumumab, amrubicin, oregovomab, Lep-etu, nolatrexed, azd2171, batabulin, ofatumumab, zanolimumab, edotecarin, tetrandrine, rubitecan, tesmilifene, oblimersen, ticilimumab, ipilimumab, gossypol, Bio 111, 131-I-TM-601, ALT-110, BIO 140, CC 8490, cilengitide, gimatecan, IL13-PE38QQR, NO 1001, IPdR$_1$ KRX-0402, lucanthone, LY 317615, neuradiab, vitespan, Rta 744, Sdx 102, talampanel, atrasentan, Xr 311, romidepsin, ADS-100380, sunitinib, 5-fluorouracil, vorinostat, etoposide, gemcitabine, doxorubicin, liposomal doxorubicin, 5'-deoxy-5-fluorouridine, vincristine, temozolomide, ZK-304709, seliciclib; PD0325901, AZD-6244, capecitabine, L-Glutamic acid, N-[4-[2-(2-amino-4,7-dihydro-4-oxo-1H-pyrrolo[2,3-d]pyrimidin-5-yl)ethyl]benzoyl]-, disodium salt, heptahydrate, camptothecin, PEG-labeled irinotecan, tamoxifen, toremifene citrate, anastrazole, exemestane, letrozole, DES(diethylstilbestrol), estradiol, estrogen, conjugated estrogen, bevacizumab, IMC-1C11, CHIR-258,); 3-[5-(methylsulfonylpiperadinemethyl)-indolylj-quinolone, vatalanib, AG-013736, AVE-0005, the acetate salt of [D-Ser(Bu t) 6, Azgly 10] (pyro-Glu-His-Trp-Ser-Tyr-D-Ser(Bu t)-Leu-Arg-Pro-Azgly-NH$_2$ acetate [$C_{59}H_{84}N_{18}Oi_4$-$(C_2H_4O_2)_x$ where x=1 to 2.4], goserelin acetate, leuprolide acetate, triptorelin pamoate, medroxyprogesterone acetate, hydroxyprogesterone caproate, megestrol acetate, raloxifene, bicalutamide, flutamide, nilutamide, megestrol acetate, CP-724714; TAK-165, HKI-272, erlotinib, lapatanib, canertinib, ABX-EGF antibody, erbitux, EKB-569, PKI-166, GW-572016, Ionafarnib, BMS-214662, tipifarnib; amifostine, NVP-LAQ824, suberoyl analide hydroxamic acid, valproic acid, trichostatin A, FK-228, SU11248, sorafenib, KRN951, aminoglutethimide, amsacrine, anagrelide, L-asparaginase, *Bacillus* Calmette-Guerin (BCG) vaccine, bleomycin, buserelin, busulfan, carboplatin, carmustine, chlorambucil, cisplatin, cladribine, clodronate, cyproterone, cytarabine, dacarbazine, dactinomycin, daunorubicin, diethylstilbestrol, epirubicin, fludarabine, fludrocortisone, fluoxymesterone, flutamide, gemcitabine, hydroxyurea, idarubicin, ifosfamide, imatinib, leuprolide, levamisole, lomustine, mechlorethamine, melphalan, 6-mercaptopurine, mesna, methotrexate, mitomycin, mitotane, mitoxantrone, nilutamide, octreotide, oxaliplatin, pamidronate, pentostatin, plicamycin, porfimer, procarbazine, raltitrexed, rituximab, streptozocin, teniposide, testosterone, thalidomide, thioguanine, thiotepa, tretinoin, vindesine, 13-cis-retinoic acid, phenylalanine mustard, uracil mustard, estramustine, altretamine, floxuridine, 5-deooxyuridine, cytosine arabinoside, 6-mecaptopurine, deoxycoformycin, calcitriol, valrubicin, mithramycin, vinblastine, vinorelbine, topotecan, razoxin, marimastat, COL-3, neovastat, BMS-275291, squalamine, endostatin, SU5416, SU6668, EMD121974, interleukin-12, IM862, angiostatin, vitaxin, droloxifene, idoxyfene, spironolactone, finasteride, cimitidine, trastuzumab, denileukin diftitox, gefitinib, bortezimib, paclitaxel, cremophor-free paclitaxel, docetaxel, epithilone B, BMS-247550, BMS-310705, droloxifene, 4-hydroxytamoxifen, pipendoxifene, ERA-923, arzoxifene, fulvestrant, acolbifene, lasofoxifene, idoxifene, TSE-424, HMR-3339, ZK186619, topotecan, PTK787/ZK 222584, VX-745, PD 184352, rapamycin, 40-O-(2-hydroxyethyl)-rapamycin, temsirolimus, AP-23573, RAD001, ABT-578, BC-210, LY294002, LY292223, LY292696, LY293684, LY293646, wortmannin, ZM336372, L-779,450, PEG-filgrastim, darbepoetin, erythropoietin, granulocyte colony-stimulating factor, zolendronate, prednisone, cetuximab, granulocyte macrophage colony-stimulating factor, histrelin, pegylated interferon alfa-2a, interferon alfa-2a, pegylated interferon alfa-2b, interferon alfa-2b, azacitidine, PEG-L-asparaginase, lenalidomide, gemtuzumab, hydrocortisone, interleukin-11, dexrazoxane, alemtuzumab, all-transretinoic acid, ketoconazole, interleukin-2, megestrol, immune globulin, nitrogen mustard, methylprednisolone, ibritgumomab tiuxetan, androgens, decitabine, hexamethylmelamine, bexarotene, tositumomab, arsenic trioxide, cortisone, editronate, mitotane, cyclosporine, liposomal daunorubicin, Edwina-asparaginase, strontium 89, casopitant, netupitant, an NK-1 receptor antagonists, palonosetron, aprepitant, diphenhydramine, hydroxyzine, metoclopramide, lorazepam, alprazolam, haloperidol, droperidol, dronabinol, dexamethasone, methylprednisolone, prochlorperazine, granisetron, ondansetron, dolasetron, tropisetron, pegfilgrastim, erythropoietin, epoetin alfa and darbepoetin alfa, among others.

Formulations containing the compounds according to the present invention may take the form of liquid, solid, semi-solid or lyophilized powder forms, such as, for example, solutions, suspensions, emulsions, sustained-release formulations, tablets, capsules, powders, suppositories, creams, ointments, lotions, aerosols, patches or the like, preferably in unit dosage forms suitable for simple administration of precise dosages. Preferably, the formulations are softgels or hard gels (most preferably softgels) or are powders Pharmaceutical compositions according to the present invention typically include a conventional pharmaceutical carrier or excipient and may additionally include other medicinal agents, carriers, adjuvants, additives and the like. The weight percentage ratio of the one or more curcuminoids, curcuminoid analogs and/or curcuminoid metabolites to the absorption enhancer is between about 20:1 to about 1:60, or between about 15:1 to about 1:45, or between about 10:1 to about 1:40, or between about 9:1, 8:1, 7:1, 6:1, 5:1, 4:1, 3:1, 2:1 or 1:1 to about 1:2, 1:3, 1:4, 1:5, 1:6, 1:7, 1:8, 1:9, 1:10, 1:15, 1:20, 1:25, 1:30, or 1:35, and preferably is about 20:1, 19:1, 18:1, 17:1, 16:1, 15:1, 14:1, 13:1, 12:1, 11:1, 10:1, 9:1, 8:1, 7:1, 6:1 or 5:1. In some embodiments, formulations of the invention comprise between about 250 mg to about 1200 mg, or between about 300 mg to about 1100 mg, or about 325 mg to about 950 mg, most preferably about 380 mg of total curcuminoids and may optionally contain one or more suitable pharmaceutical excipients.

An injectable composition for parenteral administration (e.g. intravenous, intramuscular or intrathecal) will typically contain the compound in a suitable i.v. solution, such as sterile physiological salt solution. The composition may also be formulated as a suspension in an aqueous emulsion.

Liquid compositions can be prepared by dissolving or dispersing the pharmaceutical composition comprising curcuminoids, curcuminoid analogs and/or curcuminoid metabolites, and optional pharmaceutical adjuvants, in a carrier, such as, for example, aqueous saline, aqueous dextrose, glycerol, or ethanol, to form a solution or suspension. For use in an oral liquid preparation, the composition may be prepared as a solution, suspension, emulsion, or syrup, being supplied either in liquid form or a dried form suitable for hydration in water or normal saline.

For oral administration, such excipients include pharmaceutical grades of mannitol, lactose, starch, magnesium stearate, sodium saccharine, talcum, cellulose, glucose, gelatin, sucrose, magnesium carbonate, and the like. If desired, the composition may also contain minor amounts of non-toxic auxiliary substances such as wetting agents, emulsifying agents, or buffers.

When the composition is employed in the form of solid preparations for oral administration, the preparations may be tablets, granules, powders, capsules or the like. In a tablet formulation, the composition is typically formulated with additives, e.g. an excipient such as a saccharide or cellulose preparation, a binder such as starch paste or methyl cellulose, a filler, a disintegrator, and other additives typically used in the manufacture of medical preparations.

Methods for preparing such dosage forms are known or are apparent to those skilled in the art; for example, see Remington's Pharmaceutical Sciences (17th Ed., Mack Pub. Co. 1985). The composition to be administered will contain a quantity of the selected compound in a pharmaceutically effective amount for therapeutic use in a biological system, including a patient or subject according to the present invention.

Methods of treating patients or subjects in need for a particular disease state or infection comprise administration of an effective amount of a pharmaceutical composition comprising therapeutic amounts of curcuminoids, curcuminoid analogs and/or curcuminoid metabolites and optionally at least one additional bioactive (e.g. anti-cancer) agent according to the present invention.

The amount of curcuminoids, curcuminoid analogs and/or curcuminoid metabolites used in the methods of treatment of the instant invention that may be combined with the carrier materials to produce a single dosage form will vary depending upon the host treated, the particular mode of administration. For example, the compositions could be formulated so that a therapeutically effective dosage of between about 0.01, 0.1, 1, 5, 10, 15, 20, 25, 30, 35, 40, 45, 50, 55, 60, 65, 70, 75, 80, 85, 90 or 100 mg/kg of patient/day or in some embodiments, greater than 100, 110, 120, 130, 140, 150, 160, 170, 180, 190 or 200 mg/kg of the curcuminoids, curcuminoid analogs and/or curcuminoid metabolites can be administered to a patient receiving these compositions.

Preferably, pharmaceutical compositions in dosage form according to the present invention comprise a therapeutically effective amount of at least 25 mg of curcuminoids, curcuminoid analogs and/or curcuminoid metabolites, at least 50 mg of curcuminoids, curcuminoid analogs and/or curcuminoid metabolites, at least 60 mg of curcuminoids, curcuminoid analogs and/or curcuminoid metabolites, at least 75 mg of curcuminoids, curcuminoid analogs and/or curcuminoid metabolites, at least 100 mg of curcuminoids, curcuminoid analogs and/or curcuminoid metabolites, at least 150 mg of curcuminoids, curcuminoid analogs and/or curcuminoid metabolites, at least 200 mg of curcuminoids, curcuminoid analogs and/or curcuminoid metabolites, at least 250 mg of curcuminoids, curcuminoid analogs and/or curcuminoid metabolites, at least 300 mg of curcuminoids, curcuminoid analogs and/or curcuminoid metabolites, about 350 mg of curcuminoids, curcuminoid analogs and/or curcuminoid metabolites, about 400 mg of curcuminoids, curcuminoid analogs and/or curcuminoid metabolites, about 500 mg of curcuminoids, curcuminoid analogs and/or curcuminoid metabolites, about 750 mg of curcuminoids, curcuminoid analogs and/or curcuminoid metabolites, about 380 mg of curcuminoids, curcuminoid analogs and/or curcuminoid metabolites, about 950 mg of curcuminoids, curcuminoid analogs and/or curcuminoid metabolites, about 1 g (1,000 mg) of curcuminoids, curcuminoid analogs and/or curcuminoid metabolites, about 1100 mg of curcuminoids, curcuminoid analogs and/or curcuminoid metabolites, 1200 mg of curcuminoids, curcuminoid analogs and/or curcuminoid metabolites, alone or in combination with a therapeutically effective amount of at least one additional anti-inflammatory or anti-cancer agent.

In certain embodiments of the pharmaceutical compositions of the invention, the total curcuminoids comprise between about 65 wt % to about 85 wt % curcumin (preferably between about 75 wt % to about 85 wt %); between about 10 wt % to about 30 wt % demethoxycurcumin (preferably between about 15 wt % to about 20 wt %); and between about 2 wt % to about 8 wt % bisdemethoxycurcumin (most preferably about 5 wt %).

Preferred embodiments of the pharmaceutical compositions of the invention comprise between about 250 mg to about 1200 mg, or between about 300 mg to about 1100 mg, or about 325 mg to about 950 mg, most preferably about 380 mg of total curcuminoids.

These and other aspects of the invention are illustrated further in the following non-limiting examples.

Example 1

Curcumin Softgel and Powder Formulations

Curcumin Softgel (Clinical A)
A softgel filled with one (1) gram of lipid emulsion which contains 380 mg of total curcuminoids.
The lipid emulsion consist of 1 part TPGS, 6.5 parts of turmeric oil, 4.5 parts of lecithin, and 8 parts of curcumin powder with 95% curcuminoids.
*TPGS is first melted at 65-70 degrees C. in a beaker on a stir plate. Turmeric oil and lecithin are added and stirred, followed by slow addition of turmeric powder. Formulation remains on stir plate until evenly mixed (a non-aqueous solvent may be added to mixture or the solution may be used neat, i.e., without additional solvent). Potency was determined by HPLC.
Curcumin Powder (Clinical B)
A hard gel capsule filled with 449 mg of emulsified curcumin powder containing 380 mg total curcuminoids. The emulsified powder was prepared by mixing 1 part TPGS, 19 parts of curcumin powder with 95% curcuminoids and 20 parts deionized water.
*TPGS is first melted at 65-70 degrees C. in a beaker on a stir plate. 10 mL of water at the same temperature is added and stirred until an even mixture. Curcumin powder is slowly added to make a slurry, then allowed to dry by evaporation. TPGS makes up 5% of final powder after drying. Potency was determined by HPLC.

The comparative absorption of formulations A and B was examined in the clinical study described hereinafter in Example 2.

Example 2

Comparative Absorption of Four Curcumin Formulations

Materials and Methods
Curcumin Formulations

Four formulations with 380 mg total curcuminoids per dose were used in the study. The amounts of curcumin, demethoxycurcumin and bisdemethoxycurcumin in each formulation are shown in Table 1. The DFH formulation in softgel and powder formats contained commercially available curcumin powder that was emulsified using proprietary technology. Clinical A and B were prepared as described in Example 1.

TABLE 1

Curcuminoid composition of formulations used in the study.

| Formulation | Total curcuminoids mg | Curcumin mg (%) | Demethoxycurcumin mg (%) | Bisdemethoxycurcumin mg (%) |
| --- | --- | --- | --- | --- |
| Clinical A - 1 | 380 | 295 (77.6%) | 67 (17.6%) | 18 (4.8%) |
| Clinical B - | 380 | 313 (82.5%) | 57 (14.9%) | 10 (2.6%) |
| C - Hard gel capsule with 400 mg curcumin powder (95% curcuminoids) | 380 | 302 (79.4%) | 63 (16.7%) | 15 (3.9%) |
| D - Hard gel capsule with 400 mg curcumin powder (commercial brand) | 380 | 304 (80.0%) | 62 (16.2%) | 14 (3.8%) |

Subjects

Eight healthy participants were recruited for the study (5 female and 3 male, 26-50 years). Written informed consent was obtained from all participants before inclusion in the trial. Exclusion criteria were: presence of clinically significant history of inflammatory bowel disease (i.e. ulcerative colitis, Crohn's, Celiac, etc.), ulcer, liver and kidney disease or other acute or chronic disease; use of NSAIDS, any blood thinners, H2 blockers and PPI or blood sugar-lowering agents; diabetes, hyperglycemia, hemophilia, pregnancy, and allergy to turmeric or curcumin.

Study Design

The study was a randomized crossover design with four arms (series) separated by seven day washout period. Participants were asked to maintain their regular lifestyle and to refrain from consuming any curcumin-containing supplement or food for two weeks prior to testing. The curcumin formulations were administered in the morning following a 10-hour fast. All participants orally ingested one of the randomly assigned formulations, A, B, C, or D for that period. Six mL of blood samples were collected from each participant at 0 (before curcumin ingestion), 1, 2, 4 and 8 h after ingestion of assigned formulation. Participants ate standard breakfast consisting of one bagel with plain cream cheese 30 minutes after ingesting the formulation and a standard lunch consisting of vegetable salad with chicken after the fourth blood sample was drawn (4 h after ingestion of treatment). After a washout period of seven days, the same process was repeated except for the consumption of a different formulation.

Sample Collection

During each time point, 6 mL of blood was drawn into vacutainer tubes. Blood tubes were centrifuged as 1,300×g for 10 minutes and plasma was aliquoted into cryogenic vials and immediately frozen in dry ice. Quick-frozen samples were stored at −20 C freezer until they were shipped in dry ice to a third party laboratory (Metabolic Technologies, Inc., Ames, Iowa). The samples were stored in −80 C freezer at the laboratory until analysis.

Sample Preparation and Chromatographic Analysis of the Curcuminoids

The blood plasma samples were evaluated for curcumin, demethoxycurcumin, bisdemethoxycurcumin and tetrahydrocurcumin using Agilent 1290 HPLC system with an Agilent 6460 tandem mass spectrometer with ESI source (HPLC/MS/MS; Column: Kinetex XB-C18 100 Å, 2.1×50 mm, 2.6 micron. Pre-column: security guard ultra, C18, 2.1 mm. Temperature in column chamber was set to 50° C.). Curcuminoids were extracted as follows. Serum or standard was transferred into glass tube along with 1000 U β-Glucoronidase of a 0.1M phosphate buffer (pH 6.8) and methanol. The mixture was then incubated at 37° C. for 1 hour. The internal standard Salbutamol was then added and vortexed. The curcuminoids were then extracted with 1 ml of ethyl acetate, dried, resuspended in 90:10 methanol:water and injected on the HPLC/MS/MS. Data was quantified using from linear standard curves using Agilent's Mass Hunter Software® [5].

Statistical Treatment of Data

Means and standard deviations (standard error of the mean) were calculated using Microsoft Excel. Area under concentration-time curve (AUC) for eight hours was calculated by trapezoidal rule using Microsoft Excel. Absorption of curcuminoids in Formulation A relative to those in other formulations was calculated by dividing the AUC value of a curcuminoid in Formulation A by AUC of the corresponding curcuminoid in Formulation B, C or D multiplied by the dosage of that curcuminoid in Formulation B, C or D divided by the dosage of that curcuminoid in Formulation A.

Results

Curcumin, demethoxycurcumin and bisdemethoxycurcumin were not detected in fasting plasma samples (baseline) in six of eight participants. Two participants had very low but detectable baseline concentrations of curcumin and tetrahydrocurcumin. Pharmacokinetic data of the individual curcuminoids present in the formulation (curcumin, demethoxycurcumin, bisdemethoxycurcumin) are shown in Table 2. Mean concentrations were plotted in concentration time-curves and shown in FIGS. 1-4. Concentrations are expressed in ng/mL and refer to enzymatically hydrolyzed plasma samples.

The concentrations of curcumin, demethoxycurcumin and bisdemethoxycurcumin appearing in the plasma following ingestion of Formulations A and B were higher than those of Formulations C and D (FIGS. 1-3). With Formulation A, curcumin concentration rapidly increased following its ingestion and the mean concentration was highest (23.0 ng/mL) at 2 h (FIG. 1). Concentration of absorbed curcumin in Formulation B showed increasing trend up to 8 h with observed mean concentration of 21.1 ng/mL. Absorbed curcumin concentrations following ingestion of Formulations C and D, although very low, also showed increasing trend up to 8 h.

The mean concentration of absorbed demethoxycurcumin from Formulation A increased rapidly after ingestion to 1 h with mean value of 9.2 ng/mL and then declined to a mean value of 2.6 ng/mL at 8 h (FIG. 2). Absorbed demethoxycurcumin from Formulation B showed a more gradual increase compared to that from Formulation A, with highest mean concentration of 3.7 ng/mL at 2 h. Mean concentrations of absorbed demethoxycurcumin in Formulations C and D were extremely low (FIG. 2).

Mean absorbed bisdemethoxycurcumin from Formulation A was highest at 1 h (2.6 ng/mL) and declined to 1.0 ng/mL at 8 h (FIG. 3). Mean concentration of bisdemethoxycurcumin from Formulation B was highest at 1 h (1.8 ng/mL) and declined to 0.6 ng/mL at 8 h. There was no observed appearance of bisdemethoxycurcumin from Formulation D over the 8-hour period (FIG. 3).

Tetrahydrocurcumin, a metabolite of curcumin that is not present in curcumin powder products, was shown in a recent published study to appear in the plasma following ingestion of curcumin formulations (Jager). In this study, the concentrations of tetrahydrocurcumin appearing in the plasma following the ingestion of the four formulations were measured. Tetrahydrocurcumin concentrations showed increasing trend during the whole observation period of 8 hours. Formulation A had the highest concentration of tetrahydrocurcumin with a mean of 153.3 ng/mL at 8 h compared to 81.0 ng/mL for Formulation B. Tetrahydrocurcumin from ingestion of Formulations C and D reached a peak of less than 15 ng/mL (Table 2; FIG. 5).

Relative Absorption

Area under the plasma concentration time-curve (AUC) was calculated for each of the three curcuminoid in the formulation, their total, tetrahydrocurcumin and the total of all curcuminoids appearing in the plasma (Table 3). Using AUC values, relative absorption was determined for curcumin, demethoxycurcumin, bisdemethoxycurcumin and their sum (Table 4).

Curcumin from Formulation A was 1.4× more absorbed than that in Formulation B, 14.6× more than that in Formulation C and 37.7× more than that in Formulation D. Demethoxycurcumin in Formulation A was 1.3× better absorbed than that in Formulation B, 47× more than that in Formulation C and 324× more than that in Formulation D.

Absorption of total curcuminoids (curcumin, demethoxycurcumin and bisdemethoxycurcumin) from Formulation A was 1.4× better than Formulation B, 17.4× better than Formulation C and 46.1× better than Formulation D (Table 4).

Discussion

A study by Jager et al. compared the absorption of several curcumin formulations and measured the appearance of tetrahydrocurcumin [5]. The concentrations of tetrahydrocurcumin that appeared in the plasma following ingestion of DFH Formulations A and B were much greater than those reported by Jager et al. (Table 5).

Since tetrahydrocurcumin is a metabolite of curcuminoids, any tetrahydrocurcumin that appears in the blood would have come from absorbed curcuminoids. High concentration of tetrahydrocurcumin in the bloods following ingestion of a formulation could be an indication of greater absorption of the curcuminoids present in the ingested formulation. Also, the fact that tetrahydrocurcumin showed an increasing trend during the 8 hour testing period in this study would indicate that absorbed curcuminoids may have undergone continuous metabolism.

Tetrahydrocurcumin is considered to have superior antioxidant properties [6-8]. Recently, Sabinsa introduced a tetrahydrocurcumin ingredient in the market [9]. Considering that ingestion of DFH Formulations A and B resulted in in-vivo production of significant concentrations of tetrahydrocurcumin, supplementation with tetrahydrocurcumin may not be necessary if the newly developed curcumin formulations by DFH is taken.

The health benefits of tetrahydrocurcumin are just beginning to be understood [10-14]. If tetrahydrocurcumin is indeed a health promoting compound, consumption of the newly developed curcumin formulations of DFH should provide in vivo produced tetrahydrocurcumin.

CONCLUSIONS

This small in-house clinical study showed that two newly developed curcumin formulations of DFH are better absorbed than popular commercial curcumin products. Ingestion of DFH formulations resulted in the appearance of significant concentration of tetrahydrocurcumin, a metabolite of curcuminoids. The health implications of in-vivo production of tetrahydrocurcumin are not yet fully understood. However, ingestion of a curcumin product that results in the appearance of significant amount of tetrahydrocurcumin in the blood may make supplementation with tetrahydrocurcumin unnecessary.

TABLE 2

Mean (±SEM) plasma concentrations of absorbed curcumin, demethoxycurcumin, bisdemethoxycurcumin, total absorbed curcuminoids, the metabolite tetrahydrocurcumin and total circulating curcuminoids in ng/mL following ingestion of single oral dose of 380 mg curcuminoids.

| Formulation | 0 h | 1 h | 2 h | 4 h | 8 h |
| --- | --- | --- | --- | --- | --- |
| Curcumin | | | | | |
| A | 0.0 ± 0.0 | 15.4 ± 10.6 | 23.0 ± 12.3 | 20.1 ± 14.9 | 20.0 ± 11.4 |
| B | 0.2 ± 0.4 | 5.1 ± 4.0 | 13.8 ± 18.1 | 15.0 ± 10.6 | 21.1 ± 17.4 |
| C | 0.0 ± 0.0 | 0.5 ± 0.5 | 0.8 ± 0.7 | 1.4 ± 0.8 | 2.4 ± 1.4 |
| D | 0.0 ± 0.0 | 0.3 ± 0.6 | 0.3 ± 0.5 | 0.5 ± 0.7 | 1.0 ± 0.3 |
| Demethoxycurcumin | | | | | |
| A | 0.0 ± 0.0 | 9.2 ± 4.4 | 6.3 ± 2.7 | 3.7 ± 2.7 | 2.6 ± 1.7 |
| B | 0.0 ± 0.0 | 3.1 ± 2.5 | 3.7 ± 4.6 | 3.2 ± 2.3 | 2.6 ± 3.0 |
| C | 0.0 ± 0.0 | 0.2 ± 0.3 | 0.1 ± 0.2 | 0.1 ± 0.2 | 0.1 ± 0.2 |
| D | 0.0 ± 0.0 | 0.0 ± 0.0 | 0.1 ± 0.2 | 0.0 ± 0.0 | 0.0 ± 0.0 |

TABLE 2-continued

Mean (±SEM) plasma concentrations of absorbed curcumin, demethoxycurcumin, bisdemethoxycurcumin, total absorbed curcuminoids, the metabolite tetrahydrocurcumin and total circulating curcuminoids in ng/mL following ingestion of single oral dose of 380 mg curcuminoids.

| Formulation | 0 h | 1 h | 2 h | 4 h | 8 h |
|---|---|---|---|---|---|
| Bisdemethoxycurcumin | | | | | |
| A | 0.0 ± 0.0 | 2.6 ± 1.3 | 1.5 ± 1.9 | 2.1 ± 2.0 | 1.0 ± 1.0 |
| B | 0.0 ± 0.0 | 1.8 ± 1.6 | 0.8 ± 1.2 | 0.5 ± 0.6 | 0.6 ± 1.1 |
| C | 0.0 ± 0.0 | 0.0 ± 0.0 | 0.0 ± 0.0 | 0.1 ± 0.2 | 0.0 ± 0.0 |
| D | 0.0 ± 0.0 | 0.0 ± 0.0 | 0.0 ± 0.0 | 0.0 ± 0.0 | 0.0 ± 0.0 |
| Total absorbed curcuminoids (sum of three curcuminoids present in the formulation) | | | | | |
| A | 0.0 ± 0.0 | 27.2 ± 15.6 | 30.7 ± 13.9 | 26.0 ± 18.3 | 23.8 ± 12.7 |
| B | 0.1 ± 0.4 | 10.1 ± 7.7 | 18.3 ± 23.7 | 18.8 ± 13.2 | 24.3 ± 21.3 |
| C | 0.0 ± 0.0 | 0.95 ± 1.0 | 0.9 ± 0.9 | 1.5 ± 1.0 | 2.6 ± 1.6 |
| D | 0.0 ± 0.0 | 0.3 ± 0.6 | 0.4 ± 0.8 | 0.5 ± 0.7 | 1.1 ± 0.2 |
| Tetrahydrocurcumin | | | | | |
| A | 0 | 54.4 ± 61.7 | 145.2 ± 145.6 | 129.5 ± 132.6 | 153.3 ± 170.8 |
| B | 0 | 23.3 ± 19.6 | 70.8 ± 80.8 | 53.7 ± 38.0 | 81.0 ± 103.6 |
| C | 0 | 1.25 ± 1.6 | 2.7 ± 3.6 | 6.2 ± 4.8 | 14.1 ± 9.0 |
| D | 0 | 1.3 ± 2.0 | 2.5 ± 2.3 | 3.2 ± 2.7 | 9.1 ± 6.9 |
| Total circulating curcuminoids (includes the metabolite tetrahydrocurcumin) | | | | | |
| A | 0 | 81.6 ± 74.8 | 175.9 ± 156.7 | 155.4 ± 138.7 | 177.1 ± 174.4 |
| B | 0 | 33.4 ± 25.1 | 89.1 ± 104.0 | 72.4 ± 47.6 | 105.2 ± 105.0 |
| C | 0 | 1.9 ± 2.1 | 3.6 ± 4.2 | 7.7 ± 5.6 | 16.7 ± 10.0 |
| D | 0 | 1.6 ± 2.1 | 2.8 ± 2.1 | 3.7 ± 2.8 | 10.2 ± 6.9 |

TABLE 3

Area under the concentration-time curves (AUC) for curcumin, demethoxycurcumin, bisdemethoxycurcumin, total of three curcuminoids, tetrahydrocurcumin and total circulating curcuminoids.

| Curcuminoid | Formulation | AUC 0-8 h (ng/mL) |
|---|---|---|
| Curcumin | A | 150.1 ± 87.1 |
| | B | 112.9 ± 63.9 |
| | C | 10.5 ± 5.4 |
| | D | 4.1 ± 2.2 |
| Demethoxycurcumin | A | 35.0 ± 17.0 |
| | B | 23.5 ± 16.7 |
| | C | 0.7 ± 1.0 |
| | D | 0.1 ± 0.4 |
| Bisdemethoxycurcumin | A | 13.1 ± 8.1 |
| | B | 5.6 ± 5.4 |
| | C | 0.2 ± 0.5 |
| | D | 0.1 ± 0.2 |
| Total absorbed curcuminoids (curcumin + demethoxycurcumin + bisdemethoxycurcumin) | A | 198.3 ± 103.9 |
| | B | 142.1 ± 85.0 |
| | C | 11.4 ± 6.1 |
| | D | 4.3 ± 2.6 |
| Tetrahydrocurcumin | A | 967.3 ± 972.7 |
| | B | 452.7 ± 299.2 |
| | C | 52.3 ± 30.6 |
| | D | 32.7 ± 16.3 |
| Total circulating curcuminoids (curcumin + demethoxycurcumin + bisdemethoxycurcumin + tetrahydrocurcumin) | A | 1165.5 ± 1024.9 |
| | B | 595.8 ± 355.8 |
| | C | 63.7 ± 35.2 |
| | D | 37.0 ± 15.5 |

TABLE 4

Relative absorption of four formulations tested.

| | | | Formulation A | | | |
|---|---|---|---|---|---|---|
| | mg/dose | AUC 0-8 h (ng/mL) | Curcumin | Demethoxycurcumin | Bismethoxycurcumin | Total Curcuminoids |
| | | | 295 | 67 | 18 | 380 |
| | | | 150.1 | 35.0 | 13.1 | 198.3 |
| Formulation B | | | | | | |
| Curcumin | 313 | 112.9 | 1.4 | | | |
| Demethoxycurcumin | 57 | 23.5 | | 1.3 | | |
| Bismethoxycurcumin | 10 | 5.6 | | | 1.3 | |
| Total Curcuminoids | 380 | 142.1 | | | | 1.4 |

TABLE 4-continued

Relative absorption of four formulations tested.

|  | mg/dose | AUC 0-8 h (ng/mL) | Formulation A | | | |
|---|---|---|---|---|---|---|
|  |  |  | Curcumin 295 150.1 | Demethoxycurcumin 67 35.0 | Bismethoxycurcumin 18 13.1 | Total Curcuminoids 380 198.3 |
| Formulation C |  |  |  |  |  |  |
| Curcumin | 302 | 10.5 | 14.6 |  |  |  |
| Demethoxycurcumin | 63 | 0.7 |  | 47.0 |  |  |
| Bismethoxycurcumin | 15 | 0.2 |  |  | 54.6 |  |
| Total Curcuminoids | 380 | 11.4 |  |  |  | 17.4 |
| Formulation D |  |  |  |  |  |  |
| Curcumin | 304 | 4.1 | 37.7 |  |  |  |
| Demethoxycurcumin | 62 | 0.1 |  | 323.9 |  |  |
| Bismethoxycurcumin | 14 | 0.1 |  |  | 101.9 |  |
| Total Curcuminoids | 380 | 4.3 |  |  |  | 46.1 |

TABLE 5

Comparison of AUC of Formulations A and B with published data.

| From Table 1 of Jager et al, 2014 | $AUC_{0-12h}$ (ng/mL) | Interpolated $AUC_{0-8h}$ (ng/mL) | DFH Formulation A AUC 0-8 h (ng/mL) | Relative AUC | DFH Formulation B AUC 0-8 h (ng/mL) | Relative AUC |
|---|---|---|---|---|---|---|
| CHC (OmniActive maker of CurcuWin) 376 mg total curcuminoids per dose |  |  |  | A/CHC |  | B/CHC |
| Curcumin | 307.6 | 205 | 150.1 | 0.7 | 112.9 | 0.6 |
| Demethoxycurcumin | 54.5 | 36.3 | 35 | 1.0 | 23.5 | 0.6 |
| Bismethoxycurcumin | 10.2 | 6.8 | 13.1 | 1.9 | 5.6 | 0.8 |
| Tetrahydrocurcumin | 7.7 | 5.1 | 967.3 | 188.4 | 452.7 | 88.2 |
| Total Curcuminoids (including tetrahydrocurcumin) | 380 | 253.3 | 1165.5 | 4.6 | 595.8 | 2.4 |
| CTR (Dolcas Biotech maker of BCM95) 376 mg total curcuminoids per dose |  |  |  | A/CTR |  | B/CTR |
| Curcumin | 5.8 | 3.9 | 150.1 | 38.8 | 112.9 | 29.2 |
| Demethoxycurcumin | 2.2 | 1.5 | 35 | 23.9 | 23.5 | 16.0 |
| Bismethoxycurcumin | 2.6 | 1.7 | 13.1 | 7.6 | 5.6 | 3.2 |
| Tetrahydrocurcumin | 0.3 | 0.2 | 967.3 | 4836.5 | 452.7 | 2263.5 |
| Total Curcuminoids (including tetrahydrocurcumin) | 10.9 | 7.3 | 1165.5 | 160.4 | 595.8 | 82.0 |
| CP (Indena maker of Meriva) 376 mg total curcuminoids per dose |  |  |  | A/CP |  | B/CP |
| Curcumin | 28.7 | 19.1 | 150.1 | 7.8 | 112.9 | 5.9 |
| Demethoxycurcumin | 28 | 18.7 | 35 | 1.9 | 23.5 | 1.3 |
| Bismethoxycurcumin | 6.7 | 4.5 | 13.1 | 2.9 | 5.6 | 1.3 |
| Tetrahydrocurcumin | 1.9 | 1.3 | 967.3 | 763.7 | 452.7 | 357.4 |
| Total Curcuminoids (including tetrahydrocurcumin) | 65.3 | 43.5 | 1165.5 | 26.8 | 595.8 | 13.7 |
| CS (Sabinsa, maker of C3 Complex) 1800 mg total curcuminoids per dose |  |  |  | A/CS |  | B/CS |
| Curcumin | 10.8 | 7.2 | 150.1 | 20.8 | 112.9 | 15.7 |
| Demethoxycurcumin | 18.4 | 12.3 | 35 | 2.9 | 23.5 | 1.9 |
| Bismethoxycurcumin | 9.3 | 6.2 | 13.1 | 2.1 | 5.6 | 0.9 |
| Tetrahydrocurcumin | 1.1 | 0.7 | 967.3 | 1319.0 | 452.7 | 617.3 |
| Total Curcuminoids (including tetrahydrocurcumin) | 39.6 | 26.4 | 1165.5 | 44.1 | 595.8 | 22.6 |

REFERENCES

1. Comparative absorption of a standardized curcuminoid mixture and its lecithin formulation. Cuomo J, Appendino G, Dern A S, Schneider E, McKinnon T P, Brown M J, Togni S, Dixon B M. J Nat Prod. 2011 Apr. 25; 74(4):664-9. doi: 10.1021/np1007262. Epub 2011 Mar. 17. PMID: 21413691
2. Influence of piperine on the pharmacokinetics of curcumin in animals and human volunteers. Shoba G, Joy D, Joseph T, Majeed M, Rajendran R, Srinivas P S. Planta Med. 1998 May; 64(4):353-6. PMID: 9619120
3. A Pilot Cross-Over Study to Evaluate Human Oral Bio-availability of BCM-95CG (Biocurcumax), A Novel Bio-enhanced Preparation of Curcumin. Antony B, Merina B, Iyer V S, Judy N, Lennertz K, Joyal S. Indian J Pharm Sci. 2008 July-August; 70(4):445-9. doi: 10.4103/0250-474X.44591. PMID: 20046768
4. The oral bioavailability of curcumin from micronized powder and liquid micelles is significantly increased in healthy humans and differs between sexes. Schiborr C, Kocher A, Behnam D, Jandasek J, Toelstede S, Frank J. Mol Nutr Food Res. 2014 March; 58(3):516-27. doi: 10.1002/mnfr.201300724. Epub 2014 Jan. 9. Erratum in: Mol Nutr Food Res. 2014 March; 58(3):647 PMID: 24402825
5. Comparative absorption of curcumin formulations. Jager R, Lowery R P, Calvanese A V, Joy J M, Purpura M, Wilson J M. Nutr J. 2014 Jan. 24; 13:11. doi: 10.1186/1475-2891-13-11. PMID: 24461029
6. Curcumin and especially tetrahydrocurcumin ameliorate oxidative stress-induced renal injury in mice. Okada K, Wangpoengtrakul C, Tanaka T, Toyokuni S, Uchida K, Osawa T. J Nutr. 2001 August; 131(8):2090-5. PMID: 11481399
7. Antioxidative activity of tetrahydrocurcuminoids. Osawa T, Sugiyama Y, Inayoshi M, Kawakishi S. Biosci Biotechnol Biochem. 1995 September; 59(9):1609-12. PMID: 8520105
8. Involvement of the beta-diketone moiety in the antioxidative mechanism of tetrahydrocurcumin. Sugiyama Y, Kawakishi S, Osawa T. Biochem Pharmacol. 1996 Aug. 23; 52(4):519-25. PMID: 8759023
9. Tetrahydrocurcuminoids: Product write-up bioactive antioxidant compounds from curcuminoids, Majeed M, Prakash L. Sabinsa Corporation http://www.sabinsa.com/products/standardized-phytoextracts/tetrahydrocurcuminoids/tetrahydrocurcuminoids.pdf curcuminoids, Majeed M, Prakash L. Sabinsa Corporation http://www.sabinsa.com/products/standardized-phytoextracts/tetrahydrocurcuminoids/tetrahydrocurcuminoids.pdf
10. Inhibitory effects of curcumin and tetrahydrocurcuminoids on the tumor promoter-induced reactive oxygen species generation in leukocytes in vitro and in vivo. Nakamura Y, Ohto Y, Murakami A, Osawa T, Ohigashi H. Jpn J Cancer Res. 1998 April; 89(4):361-70. PMID: 9617340
11. Chemopreventative effects of tetrahydrocurcumin on human diseases. Wu J C, Tsai M L, Lai C S, Wang Y J, Ho C T, Pan M H. Food Funct. 2014 January; 5(1):12-7. doi: 10.1039/c3fo60370a. PMID: 24220621
12. Tetrahydrocurcumin is more effective than curcumin in preventing azoxymethane-induced colon carcinogenesis. Lai C S, Wu J C, Yu S F, Badmaev V, Nagabhushanam K, Ho C T, Pan M H. Mol Nutr Food Res. 2011 December; 55(12):1819-28. doi: 10.1002/mnfr.201100290. Epub 2011 Sep. 2. PMID: 21887819
13. Tetrahydrocurcumin extends life span and inhibits the oxidative stress response by regulating the FOXO forkhead transcription factor. Xiang L, Nakamura Y, Lim Y M, Yamasaki Y, Kurokawa-Nose Y, Maruyama W, Osawa T, Matsuura A, Motoyama N, Tsuda L. Aging (Albany N.Y.). 2011 November; 3(11):1098-109. PMID: 22156377
14. Bioactivity of turmeric-derived curcuminoids and related metabolites in breast cancer. Wright L E, Frye J B, Gorti B, Timmermann B N, Funk J L. Curr Pharm Des. 2013; 19(34):6218-25. PMID: 23448448

Issued Patents

| | |
|---|---|
| United States Patent | 8,785,380 |
| Madhavamenon, et al. | Jul. 22, 2014 |
| Formulation containing curcuminoids exhibiting enhanced bioavailability | |
| United States Patent | 8,772,265 |
| Neven, et al. | Jul. 8, 2014 |
| Water soluble curcumin compositions for use in anti-cancer and anti-inflammatory therapy | |
| United States Patent | 8,748,494 |
| Diaz Alperi, et al. | Jun. 10, 2014 |
| Method for improving the therapeutic efficacy of curcuminoids and their analogs | |
| United States Patent | 8,680,143 |
| Chaniyilparampu, et al. | Mar. 25, 2014 |
| Orally active curcuminoid compounds | |
| United States Patent | 8,632,815 |
| Nair, et al. | Jan. 21, 2014 |
| Process for nanoemulsification of curcumin and derivatives of curcumin | |
| United States Patent | 8,568,815 |
| Parkkinen | Oct. 29, 2013 |
| Soluble complexes of curcumin | |
| United States Patent | 8,568,802 |
| Gokaraju, et al. | Oct. 29, 2013 |
| Process for producing enriched fractions of tetrahydroxycurcumin and tetrahydrotetrahydroxy-curcumin from the extracts of *Curcuma longa* | |
| United States Patent | 8,487,139 |
| Raja, et al. | Jul. 16, 2013 |
| Please see images for: (Certificate of Correction) | |
| Curcumin and tetrahydrocurcumin derivatives | |
| United States Patent | 8,440,245 |
| Johns, et al. | May 14, 2013 |
| Methods for making nutritional compositions comprising curcuminoids | |
| United States Patent | 8,329,757 |
| Chen | Dec. 11, 2012 |
| Curcumin analog compositions and related methods | |
| United States Patent | 8,329,233 |
| Antony | Dec. 11, 2012 |
| Composition to enhance the bioavailability of curcumin | |
| United States Patent | 8,197,869 |
| Antony | Jun. 12, 2012 |
| Composition to enhance the bioavailability of curcumin | |
| United States Patent | 8,153,172 |
| Antony | Apr. 10, 2012 |
| Composition to enhance the bioavailability of curcumin | |
| United States Patent | 7,968,115 |
| Kurzrock, et al. | Jun. 28, 2011 |
| Liposomal curcumin for treatment of cancer | |
| United States Patent | 7,883,728 |
| Antony | Feb. 8, 2011 |
| Composition to enhance the bioavailability of curcumin | |
| United States Patent | 7,879,373 |
| Antony | Feb. 1, 2011 |
| Composition to enhance the bioavailability of curcumin | |
| United States Patent | 7,736,679 |
| Antony | Jun. 15, 2010 |
| Composition to enhance the bioavailability of curcumin | |
| United States Patent | 7,682,636 |
| Babish, et al. | Mar. 23, 2010 |
| Curcuminoid compositions exhibiting synergistic inhibition of the expression and/or activity of cyclooxygenase-2 | |
| United States Patent | 7,220,438 |
| Quintanilla Almagro, et al. | May 22, 2007 |
| Pharmacological activities of *Curcuma longa* extracts | |

-continued

| | | |
|---|---|---|
| United States Patent | 7,060,733 | |
| Pandol, et al. | Jun. 13, 2006 | |
| Methods for treating pancreatitis with curcumin | | |
| compounds and inhibitors of reactive oxygen species | | |
| United States Patent | 6,979,470 | |
| Babish, et al. | Dec. 27, 2005 | |
| Curcuminoid compositions exhibiting synergistic | | |
| inhibition of the expression and/or activity of cyclooxygenase-2 | | |
| United States Patent | 6,440,468 | |
| Quintanilla Almagro, et al. | Aug. 27, 2002 | |
| Method for obtaining apolar and polar extracts of | | |
| *curcuma* and applications thereof | | |
| United States Patent | 5,266,344 | |
| Mimura, et al. | Nov. 30, 1993 | |
| Method for making tetrahydrocurcumin and a substance | | |
| containing the antioxidative substance tetrahydrocurcumin. | | |
| Patent applications | | |
| United States Patent Application | 20140295005 | |
| Kind Code | A9 | |
| Antony; Benny | Oct. 2, 2014 | |
| Formulation of Curcumin With Enhanced Bioavailability | | |
| of Curcumin and Method of Preparation and Treatment Thereof | | |
| United States Patent Application | 20140228318 | |
| Kind Code | A1 | |
| Chauhan; Subhash; et al. | Aug. 14, 2014 | |
| Curcumin formulations and methods for making such formulations | | |
| United States Patent Application | 20140193533 | |
| Kind Code | A1 | |
| ANTONY; Benny | Jul. 10, 2014 | |
| Formulation of Curcuminoids with Enhanced Bioavailability of | | |
| Curcumin, Demethoxycurcumin, Bisdemethoxycurcumin and method | | |
| of preparation and uses thereof | | |
| United States Patent Application | 20140161915 | |
| Kind Code | A1 | |
| Payne; Adam J.; et al. | Jun. 12, 2014 | |
| Solubilization of cucurminoid compounds and products thereof | | |
| United States Patent Application | 20140099390 | |
| Kind Code | A1 | |
| sssAntony; Benny | Apr. 10, 2014 | |
| Formulation of Curcumin With Enhanced Bioavailability | | |
| of Curcumin and Method of Preparation and Treatment Thereof | | |
| United States Patent Application | 20140093594 | |
| Kind Code | A1 | |
| ANTONY; Benny | Apr. 3, 2014 | |
| Composition to Enhance the Bioavailability of Curcumin | | |
| United States Patent Application | 20140088200 | |
| Kind Code | A1 | |
| ANTONY; Benny | Mar. 27, 2014 | |
| Composition to Enhance the Bioavailability of Curcumin | | |
| United States Patent Application | 20140031403 | |
| Kind Code | A1 | |
| Gately; Stephen T.; et al. | Jan. 30, 2014 | |
| Solid Forms of Curcumin | | |
| United States Patent Application | 20140010903 | |
| Kind Code | A1 | |
| Madhavamenon; Krishnakumar Illathu; et al. | Jan. 9, 2014 | |
| Curcuminoid composition with enhanced bioavailability | | |
| and a process for its preparation | | |
| United States Patent Application | 20130225689 | |
| Kind Code | A1 | |
| Khamar; Bakulesh Mafatlal; et al. | Aug. 29, 2013 | |
| PHARMACEUTICAL COMPOSITIONS OF CURCUMIN | | |
| United States Patent Application | 20130143969 | |
| Kind Code | A1 | |
| Liu; Zhongfa; et al. | Jun. 6, 2013 | |
| CURCUMIN COMPOSITIONS AND USES THEREOF | | |
| United States Patent Application | 20130029905 | |
| Kind Code | A1 | |
| Madhavamenon; Krishnakumar Illathu; et al. | Jan. 31, 2013 | |
| FORMULATION CONTAINING CURCUMINOIDS EXHIBITING | | |
| ENHANCED BIOAVAILABILITY | | |
| United States Patent Application | 20120288555 | |
| Kind Code | A1 | |
| Awasthi; Vibhudutta; et al. | Nov. 15, 2012 | |
| ANTIPROLIFERATIVE COMPOSITIONS | | |
| COMPRISING CURCUMIN ANALOGS AND METHODS OF | | |
| PRODUCING AND USING SAME | | |
| United States Patent Application | 20120220666 | |
| Kind Code | A1 | |
| Antony; Benny | Aug. 30, 2012 | |
| Composition to enhance the bioavailability of curcumin | | |
| United States Patent Application | 20120207863 | |
| Kind Code | A1 | |
| Antony; Benny | Aug. 16, 2012 | |
| Composition to enhance the bioavailability of curcumin | | |
| United States Patent Application | 20110212142 | |
| Kind Code | A1 | |
| Chaniyilparampu; Ramchand Nanappan; et al. | Sep. 1, 2011 | |
| CURCUMINOIDS AND ITS METABOLITES FOR THE | | |
| APPLICATION IN OCULAR DISEASES | | |
| United States Patent Application | 20110190399 | |
| Kind Code | A1 | |
| Kar; Santosh Kumar; et al. | Aug. 4, 2011 | |
| CURCUMIN NANOPARTICLES AND METHODS OF PRODUCING | | |
| THE SAME | | |
| United States Patent Application | 20110160276 | |
| Kind Code | A1 | |
| Namboothiri; Irishi N. N.; et al. | Jun. 30, 2011 | |
| CURCUMIN DERIVATIVES | | |
| United States Patent Application | 20100247734 | |
| Kind Code | A1 | |
| Johns; Paul W.; et al. | Sep. 30, 2010 | |
| Methods for Making Nutritional Compositions Comprising Curcuminoids | | |
| United States Patent Application | 20100179103 | |
| Kind Code | A1 | |
| Desai; Ketan | Jul. 15, 2010 | |
| CURCUMIN CYCLODEXTRIN COMBINATION FOR PREVENTING | | |
| OR TREATING VARIOUS DISEASES | | |
| United States Patent Application | 20080226755 | |
| Kind Code | A1 | |
| Antony; Benny | Sep. 18, 2008 | |
| Composition to enhance the bioavailability of curcumin | | |

What is claimed is:

1. A pharmaceutical composition comprising:
   (a) an effective amount of one or more curcuminoids, curcuminoid analogs and/or curcuminoid metabolites between 250 mg and 500 mg;
   (b) an absorption enhancer selected from the group consisting of a polyalkylene glycol derivative of vitamin E selected from the group consisting of tocopheryl polyethylene glycol succinate (TPGS), tocopheryl polyethylene glycol sebacate, tocopheryl polyethylene glycol dodecanodioate, tocopheryl polyethylene glycol suberate, tocopheryl polyethylene glycol azelaate, tocopheryl polyethylene glycol citraconate, tocopheryl polyethylene glycol methylcitraconate, tocopheryl polyethylene glycol itaconate, tocopheryl polyethylene glycol maleate, tocopheryl polyethylene glycol glutarate, tocopheryl polyethylene glycol glutaconate, tocopheryl polyethylene glycol fumarate, tocopheryl polyethylene glycol phthalate, tocotrienol polyethylene glycol succinate, tocotrienol polyethylene glycol sebacate, tocotrienol polyethylene glycol dodecanodioate, tocotrienol polyethylene glycol suberate, tocotrienol polyethylene glycol azelate, tocotrienol polyethylene glycol citraconate, tocotrienol polyethylene glycol methylcitraconate, tocotrienol polyethylene glycol itaconate, tocotrienol polyethylene glycol maleate, tocotrienol polyethylene glycol glutarate, tocotrienol polyethylene glycol glutaconate, tocotrienol polyethylene glycol fumarate and tocotrienol polyethylene glycol phthalate and mixtures thereof;
   (c) lecithin as a water-in-oil emulsifier;
   (d) essential oil of *Curcuma longa* L. (turmeric oil); and
   (e) optionally, one or more additional, pharmaceutically-acceptable excipients;

wherein the weight percentage ratio of the one or more curcuminoids, curcuminoid analogs and/or curcuminoid metabolites to the absorption enhancer is between 20:1 and 1:1 and the total curcuminoids comprise between 50 wt % and 95 wt % of curcumin; between 2 wt % and 50 wt % of demethoxycurcumin; and between 0.1 wt % and 20 wt % bisdemethoxycurcumin.

2. The composition of claim 1 wherein said TPGS is TPGS-1000.

3. The pharmaceutical composition of claim 1, wherein the total curcuminoids comprise between 65 wt % and 85 wt % of curcumin, between 10 wt % and 30 wt % of demethoxycurcumin, and between 2 wt % and 8 wt % of bisdemethoxycurcumin.

4. The pharmaceutical composition of claim 1, wherein the composition is a powder comprising one or more curcuminoids and, optionally, one or more additional, pharmaceutically-acceptable excipients.

5. The pharmaceutical composition of claim 3, wherein the composition is a powder comprising one or more additional, pharmaceutically-acceptable excipients.

6. The pharmaceutical composition of claim 4, wherein the powder comprises:
 (a) between 2 wt % and 8 wt % of the polyalkylene glycol derivative of vitamin E; and
 (b) optionally, one or more additional, pharmaceutically-acceptable excipients.

7. The pharmaceutical composition of claim 1, wherein the weight percentage ratio of the one or more curcuminoids, curcuminoid analogs and/or curcuminoid metabolites to the polyalkylene derivative of vitamin E is about 20:1.

8. The pharmaceutical composition of claim 4, wherein the total curcuminoids comprise between 75 wt % and 95 wt % of curcumin; between 5 wt % and 25 wt % of demethoxycurcumin; and between 1 wt % and 5 wt % of bisdemethoxycurcumin.

9. The pharmaceutical composition of claim 4, wherein the polyalkylene glycol derivative of vitamin E is tocotrienol polyethylene glycol succinate.

10. The pharmaceutical composition of claim 4, wherein the polyalkylene glycol derivative of vitamin E is tocopheryl polyethylene glycol succinate (TPGS).

11. The pharmaceutical composition of claim 10 wherein said polyalkylene glycol derivative of vitamin E is tocopheyl polyethylene glycol succinate-1000 (TPGS-1000).

12. The pharmaceutical composition of claim 1, wherein the composition is a softgel or hard gel capsule comprising:
 (a) between 2 wt % and 8 wt % of Vitamin E-TPGS;
 (b) between 12 wt % and 32 wt % of lecithin;
 (c) between 22 wt % and 42 wt % of essential oil of *Curcuma longa* L. (turmeric oil);
 (d) between 250 mg and 500 mg of total curcuminoids which consist essentially of 65 wt % to 85 wt % of curcumin, between 10 wt % and 30 wt % of demethoxycurcumin and between 2 wt % and 8 wt % of bisdemethoxycurcumin; and
 (e) optionally, one or more additional, pharmaceutically-acceptable excipients.

13. The pharmaceutical composition of claim 1, wherein the composition is a powder comprising:
 (a) between 250 mg and 500 mg of total curcuminoids which consist essentially of 65 wt % to 85 wt % of curcumin, between 5 wt % and 15 wt % of demethoxycurcumin and between 1 wt % and 5 wt % of bisdemethoxycurcumin;
 (b) Vitamin E-TPGS; and
 (c) optionally, one or more additional, pharmaceutically-acceptable excipients;
 wherein the weight percentage ratio of the total curcuminoids to Vitamin E-TPGS is 10:1 to 20:1.

14. The pharmaceutical composition of claim 1, wherein at eight to ten hours after oral administration to a human subject, tetrahydrocurcumin levels of between 1 ng/ml and 324.1 ng/ml are detectable in the subject's plasma.

15. The pharmaceutical composition of claim 1, wherein at eight to ten hours after oral administration to a human subject, tetrahydrocurcumin levels of between 1 ng/ml and 200 ng/ml are detectable in the subject's plasma.

16. The pharmaceutical composition of claim 1, wherein at eight to ten hours after oral administration to a human subject, tetrahydrocurcumin levels of between 50 ng/ml and 175 ng/ml are detectable in the subject's plasma.

17. The composition of claim 1, wherein the weight percentage ratio of the one or more curcuminoids, curcuminoid analogs and/or curcuminoid metabolites to the absorption enhancer is between 15:1 to 1:1.

18. The composition of claim 1, wherein the weight percentage ratio of the one or more curcuminoids, curcuminoid analogs and/or curcuminoid metabolites to the absorption enhancer is between 10:1 and 1:1.

19. The composition according to claim 1, wherein the absorption enhancer is Vitamin E-TGPS.

20. The composition according to claim 12 wherein the Vitamin E-TGPS is Vitamin E-TGPS-1000.

* * * * *